(12) United States Patent
Kariman

(10) Patent No.: US 10,751,380 B2
(45) Date of Patent: *Aug. 25, 2020

(54) COMPOUND AND METHOD FOR TREATING SPASMS, INFLAMMATION AND PAIN

(71) Applicant: Alexander Kariman, Rockville, MD (US)

(72) Inventor: Alexander Kariman, Rockville, MD (US)

(*) Notice: Subject to any disclaimer, the term of this patent is extended or adjusted under 35 U.S.C. 154(b) by 221 days.

This patent is subject to a terminal disclaimer.

(21) Appl. No.: 15/915,065

(22) Filed: Mar. 8, 2018

(65) Prior Publication Data

US 2018/0193399 A1 Jul. 12, 2018

(51) Int. Cl.

| A61K 36/00 | (2006.01) |
|---|---|
| *A61K 36/74* | (2006.01) |
| *A61K 36/185* | (2006.01) |
| *A23L 33/105* | (2016.01) |
| *A61K 9/00* | (2006.01) |
| *A61K 31/4375* | (2006.01) |
| *A61K 31/437* | (2006.01) |
| *A61K 31/352* | (2006.01) |
| *A61K 45/06* | (2006.01) |

(52) U.S. Cl.
CPC ............ *A61K 36/74* (2013.01); *A23L 33/105* (2016.08); *A61K 9/0056* (2013.01); *A61K 31/352* (2013.01); *A61K 31/437* (2013.01); *A61K 31/4375* (2013.01); *A61K 36/185* (2013.01); *A61K 45/06* (2013.01); *A23V 2002/00* (2013.01)

(58) Field of Classification Search
CPC .................................................... A61K 36/00
USPC ....................................................... 424/725
See application file for complete search history.

(56) References Cited

U.S. PATENT DOCUMENTS

| 7,449,589 B2 | 11/2008 | Geiser |
| 7,968,594 B2 | 6/2011 | Guy |
| 13,024,298 | 6/2013 | Holaday |
| 15,032,070 | 5/2018 | Takayama |
| 2006/0135599 A1 | 6/2006 | Symonds |
| 2011/0245287 A1 | 10/2011 | Holaday |

OTHER PUBLICATIONS

Kruegel, A. C., Gassaway, M. M., Kapoor, A., Váradi, A., Majumdar, S., Filizola, M., . . . Sames, D. (2016). Synthetic and Receptor Signaling Explorations of the Mitragyna. J Am Chem Soc., 138(21), 6754-64. doi:10.1021/jacs.6b00360.
Yamamoto, L. T., Horie, S., Takayama, H., Aimi, N., Sakai, S., Yano, S., . . . Watanabe, K. (1999). Opioid receptor agonistic characteristics of mitragynine pseudoindoxyl in comparison with mitragynine derived from Thai medicinal plant Mitragyna speciosa. Gen Pharmacol, 33(1), 73-81.
Macko, E, Weisbach, J. A., & Douglas, B. (1972). Some observations on the pharmacology of mitragynine. Arch. Int. Pharmacodyn. Ther., 198, 145-161.
Chittrakarn, S., Keawpradub, N., Sawangjaroen, K., Kansenalak, S., & Benjamas, J. (2010). The neuromuscular blockade produced by pure alkaloid, mitragynine and methanol extract of kratom leaves (Mitragyna speciosa Korth.). Journal of Ethnopharmacology, 129, 344-349.
Formukong, E. A., Evans, A. T., & Evans, F. J. (Aug. 1988). Analgesic and antiinflammatory activity of constituents of Cannabis sativa L. PubMed, 12(4), 361-371.
Hassana, Z., Muzaimi, M., Navaratnama, V., Yusoff, N. H., Suhaimi, F. W., Vadivelua, R., . . . Müller, C. P. (2013). From Kratom to mitragynine and its derivatives: Physiological and behavioral effects related to use, abuse, and addiction. Neuroscience and Biobehavioral Reviews, 37, 138-151.
Ramanathan, S., Parthasarathy, S., Murugaiyah, V., Magosso, E., Tan, S. C., & Mansor, S. M. (2015). Understanding the Physicochemical Properties of Mitragynine, a Principal Alkaloid of Mitragyna speciosa, for Preclinical Evaluation. Molecules, 20, 4915-4927. doi:10.3390/molecules20034915.
Trakulsrichai, S., Sathirakul, K., Auparakkitanon, S., Krongvorakul, J., Sueajai, J., Noumjad, Ni., . . . Wananukul, W. (2015). Pharmacokinetics of mitragynine in man. Drug Des Devel Ther, 9, 2421-2429. doi:10.2147/DDDT.S79658.
Wade, D. T., Makela, P. M., House, H., Bateman, C., & Robson, P. (2006). Long-term use of a cannabis-based medicine in the treatment of spasticity and other symptoms in multiple sclerosis. Multiple Sclerosis, 12, 639-645.
Lemberger, L., Martz, R., Rodda, B., Forney, R., & Rowe, H. (1973). Comparative Pharmacology of Δ9-Tetrahydrocannabinol and its Metabolite, 11-OH-Δ9-Tetrahydrocannabinol. The Journal of Clinical Investigation, 52 (10), 2411-2417. doi:10.1172/JCI107431.
Grinspoon, L., & Bakalar, J. B. (1993). Marihuana: The Forbidden Medicine. New Haven: Yale University Press.
Sallan, S. E., Zinberg, N. E., & Frei, E. (1975). Antiemetic effect of delta-9-tetrahydrocannabinol in patients receiving cancer chemotherapy. New England Journal of Medicine, 293, 795-797.
Plasse, T. F., Goiter, R. W., Krasnow, S. H., Lane, M., Shepard, K. V., & Wadleigh, R. G. (1991). Recent clinical experience with dronabinol. Pharmacology Biochemistry and Behavior, 40(3), 695-700. doi:10.1016/0091-3057(91) 90385-F.
Thompson, G. R., Rosenkrantz, H., Schaeppi, U. H., & Braude, M. C. (1973). Comparison of acute oral bxicity of cannabinoids in rats, dogs and monkeys_ Toxicology and Applied Pharmacology, 25, 363-372.
Chan, P. C., Sills, R. C., Braun, A. G., Haseman, J. K., & Bucher, J. R. (1996). Toxicity and carcinogenicity of delta 9-tetrahyrocanncinol in Fischer rats and B6C3F1 mice. Fundamentals and Applied Toxicology, 109-117.

(Continued)

*Primary Examiner* — Michael V Meller

(57) ABSTRACT

The disclosed invention generally relates to pharmaceutical and nutraceutical compounds and methods for reducing inflammation, muscle spasms, and pain associated with cancer, trauma, medical procedure, neurological diseases and disorders, as well as other conditions in subjects in need thereof. The disclosed invention further relates to *Mitragyna speciose* and *Cannabis sativa* based compounds and synthetic analogs of the alkaloids found in said plants, where said compounds can also contain a pharmacologically inactive substance for modifying certain qualities of said compounds.

1 Claim, 7 Drawing Sheets

(56) References Cited

OTHER PUBLICATIONS

Fitzgerald, K. T., Bronstein, A. C., & Newquist, K. L. (2013). Marijuana poisoning. Top Companion Anim Med., 8-12. doi:10.1053/j.tcam.2013.03.004.

Kalant, H. (2004). Adverse effects of cannabis on health: an update of the literature since 1996. Prog Neuropsychopharmacol Biol Psychiatry, 28(5), 849-863. doi:10.1016/j.pnpbp.2004.05.027.

Janchawee, B., Keawpradub, N., Cittrakarn, S., Prasettho, S., Wararatananurak, P., & Sawangjareon, K. (2007). A high-performance liquid chromatographic method for determination of mitragynine in serum and its application to a pharmacokinetic study in rats. Biomed. Chromatogr., 21, 176-183.

Azizi, J., Ismail, S., Mordi, M. N., & Ramanathan, S. (2010). In vitro and in vivo effects of three different Mitragyna speciosa Korth leaf extracts on phase II drug metabolizing enzymes—glutathione transferases (GSTs). Molecules, 15, 432-441.

Vicknasingam, B., Narayanan, S., Beng , G. T., & Mansor, S. M. (2010). The informal use of ketum (Mitragyna speciosa) for opioid withdrawal in the northern states of peninsular Malaysia and implications for drug substitution therapy. Int. J. Drug Policy, 21, 283-288. doi:10.1016/j.drugpo.2009.12.003.

Sabetghadam, A., Ramanathan , S., Sasidharan, S., & Mansor, S. M. (2013). Subchronic exposure to mitragynine, the principal alkaloid of Mitragyna speciosa, in rats. J. Ethnopharmacol, 146, 815-823. doi:10.1016/j. ep.2013.02.008.

Shaik Mossadeq, W. M., Sulaiman, M. R., Tengku Mohamad, T. A., Chiong, H. S., Baharuldin, M.T.H., Israf, D.A., M. T., Baharuldin, M. T., & Israf, D. A. (2009). Anti-inflammatory and antinociceptive effects of Mitragyna speciosa Korth methanolic extract. Medical Principles and Practice, 18, 378-384.

Kumarnsit, E., Keawpradub, N., & Nuankaew, W. (2006). Acute and long-term effects of alkaloid extract of Mitragyna speciosa on food and water intake and body weight in rats. Fitoterapia, 77, 339-345.

Harizal, S. N., Mansor, S. M., Hasnan, J., Tharakan, J. K, & Abdullah, J. (2010). Acute toxicity study of _he standardized methanolic extract of Mitragyna speciosa Korth in rodent. Journal of Ethnopharmacology, 2, 404-409.

Robson, R (2001). Therapeutic aspects of cannabis and cannabinoids. The British Journal of Psychiatry, 178, 107-115.

Noyes, R. J., Brunk, S. F., & Avery, D. A. (1975). The analgesic properties of delta-9-tetrahydrocannabinol and codeine. Clinical Pharmacology and Therapeutics, 18, 84-89.

Jain, A. K., Ryan, J. R., & Mcmahon, F. G. (1981). Evaluation of intramuscular levonantradol and placebo in acute postoperative pain. Journal of Clinical Pharmacology, 21((suppl. 8-9)), 320S-326S.

Maurer, M., Henn, V., & Dittrich, A. (1990). Delta-9-tetrahydrocannabinol shows antispastic and analgesic effects in a single case double-blind trial. European Archives of Psychiatry and Clinical Neuroscience, 240, 1-4.

Holdcroft, A., Smith, M., & Jacklin, A. (1997). Pain relief with oral cannabinoids in familial Mediterranean fever. Anaesthesia, 12, 44-49.

COMPOUND AND METHOD FOR TREATING SPASMS, INFLAMMATION AND PAIN

First Named Inventor: Alexander Kariman

| Alkaloid | Percentage | Effect |
| --- | --- | --- |
| Mitragynine | 66% | Analgesic, antitussive, antidiarrheal, adrenergic, antimalarial |
| Paynantheine | 9% | Smooth muscle relaxer |
| Speciogynine | 7% | Smooth muscle relaxer |
| 7-Hydroxymitragynine | 2% | Analgesic, antitussive, antidiarrheal |
| Speciociliatine | 1% | Weak opioid agonist |
| Mitraphylline | <1% | Vasodilator, antihypertensive, muscle relaxer, diuretic, antiamnesic, immunostimulant, anti-leukemic |
| Isomitraphylline | <1% | Immunostimulant, anti-leukemic |
| Speciophylline | <1% | Anti-leukemic |
| Rhynchophylline | <1% | Vasodilator, antihypertensive, calcium channel blocker, antiaggregant, anti-inflammatory, antipyretic, anti-arrhythmic, antithelmintic |
| Isorhynchophylline | <1% | Immunostimulant |
| Ajmalicine | <1% | Cerebrocirculant, antiaggregant, anti-adrenergic, sedative, anticonvulsant, smooth muscle relaxer |
| Corynantheidine | <1% | Opioid agonist |
| Corynoxine A | <1% | Calcium channel blocker, anti-locomotive |
| Corynoxine B | <1% | Anti-locomotive |
| Mitrafoline | <1% | |
| Isomitrafoline | <1% | |
| Oxindale A | <1% | |
| Oxindole B | <1% | |
| Speciofoline | <1% | Analgesic, antitussive |
| Isospeciofoline | <1% | |
| Ciliaphylline | <1% | Analgesic, antitussive |
| Mitraciliatine | <1% | |
| Mitragynaline | <1% | |
| Mitragynalinic acid | <1% | |
| Corynantheidalinic acid | <1% | |

Figure 2

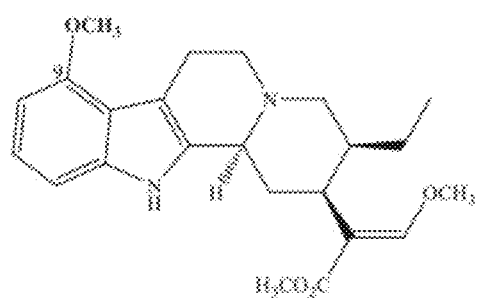
Mitragynine
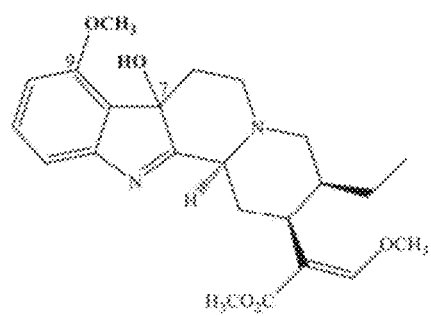
7-OH-mitragynine
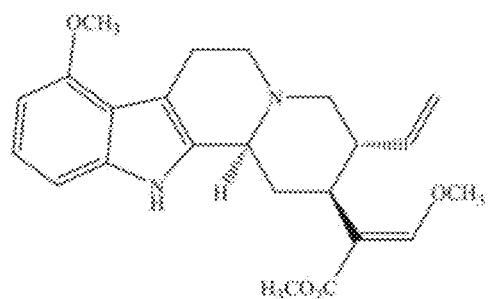
Paynantheine
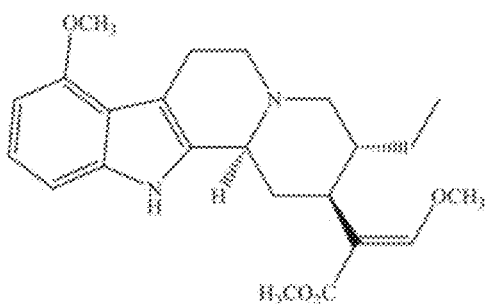
Speciogynine
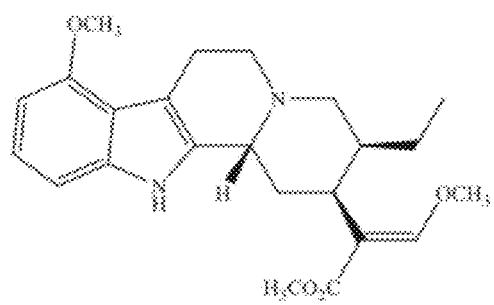
Speciociliatine
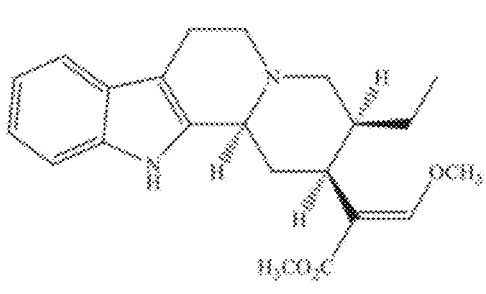
Corynantheidine
Figure 5

COMPOUND AND METHOD FOR TREATING SPASMS, INFLAMMATION AND PAIN

FIELD OF THE INVENTION

The present invention relates to pharmaceutical and nutraceutical compounds and methods for reducing spasms, inflammation, and treating pain associated with cancer, trauma, medical procedure, and neurological diseases and disorders in subjects in need thereof.

BACKGROUND OF THE INVENTION

The compounds and methods proposed by this invention are related to essentially a mixture of naturally accruing and other substances to produce a novel compound that exhibits strong anti-inflammatory, muscle relaxant, and analgesic qualities. A plurality of medicinal concoctions can be manufactured from said compound that have various pharmacological effects and different routes and methods of administration. The active ingredients of said compounds can be derived from *Mitragyna speciosa* (Kratom) and *Cannabis sativa* plants or can be chemically synthesized.

*Mitragyna speciosa* is an evergreen tree of the coffee (Rubiaceae) family native to Indonesia, Malaysia, Myanmar, Papua New Guinea, Indonesia, and Thailand. It is best known for generating leaves that contain more than 40 distinct psychoactive compounds. *Mitragyna speciosa* plant is a 4 to 16-meter-high tropical tree indigenous to South East Asia but now cultivated elsewhere. In Thailand, the tree and leaf preparations are called Kratom. Traditionally, fresh or dried Kratom leaves are chewed or made into a tea; they are seldom smoked. At a low dose, Kratom has stimulant effects and it is used to combat fatigue during long working hours. At high dosages, however, it has sedative-narcotic effect. It is also used in traditional medicine and as an opium substitute.

As already mentioned, the phytochemicals isolated from various parts of the tree include over 40 structurally related alkaloids as well as several flavonoids, terpenoid saponins, polyphenols, and various glycosides. The main psychoactive components in the leaves are mitragynine and 7-hydroxymitragynine, both found only in *Mitragyna speciosa*. Kartom contains other central nervous system stimulants and depressants that can act upon a variety of neurotransmitter systems within the human brain. As already mentioned, it has traditionally been consumed as a leaves decoction for its stimulant effects to counter fatigue, treat fever, diarrhea, as well as anesthetic, antinociceptive, analgesic and stimulating effects that help to combat fatigue and suppress appetite.

*Cannabis sativa* (marijuana) is an annual herbaceous flowering plant indigenous to eastern Asia but now of cosmopolitan distribution due to cultivation. It is placed in the *Cannabis* genus classification, which belongs to a small but diverse family, the Cannabaceae. Cannabinoid (CB) components of marijuana are known to exert behavioral and psychotropic effects but also to possess therapeutic properties including analgesia, ocular hypotension, and antiemesis. CBs-based medications are now being used for treatment of a wide range of medical conditions, including neuropathic pain, pain related to cancer and trauma, spasticity associated with Multiple Sclerosis (MS), fibromyalgia, and others.

This invention generally relates to pharmaceutical compounds and methods for reducing muscle fatigue and spasticity, reducing inflammation, and treating pain associated with cancer, trauma, medical procedure, and neurological diseases and disorders in subjects in need thereof, as well as a method of administering therapeutically-effective amount of said pharmaceutical compound containing certain natural and/or synthetic *Mitragyna speciosa* and *Cannabis sativa* alkaloids and/or their derivatives/analogs and other substances.

Other medical conditions are also contemplated by this invention that include, but are not limited to: Huntington's Disease (HD); Wilson's Disease; Parkinson's Disease (PD); metabolic and endocrine diseases and disorders; athetosis-related to damage or degeneration of basal ganglia; minor tranquilizers, alcohol, cocaine, (meta)amphetamine, and opioid withdrawal syndromes; symptoms or side effects associated with anti-retroviral therapy, chemotherapy and radiation therapy; AIDS; rheumatoid arthritis; osteoarthritis; fibromyalgia; pain and spasticity associated with MS, Neuromuscular Junction Disorder and other neurodegenerative disease, autoimmune diseases and disorders, motor neuron diseases and disorders, neurodegenerative diseases and disorders; pain associated with cancer; trauma; athletic performance; migraine; surgical intervention or medical treatment; dental and gum pain; stroke; heart attack; abdominal pain; bone pain, muscle pain; neurological pain; stomach ulcers-related pain; gallbladder disease-related pain; Central Pain Syndrome; chronic pain disorder (nociceptive pain, neuropathic pain, chronic back or leg pain, painful neuropathies, Complex Regional Pain Syndrome), and acute pain.

The principal mechanism of Kratom's psychoactive action involves mu-opioid receptor partial agonism, and to a lesser extent, kappa-opioid receptor antagonism—relatively analogous to the drug buprenorphine. Other, less prominent, mechanisms of Kratom's action include: delta-opioid receptor antagonism, alpha-2 receptor agonism, 5-HT2A receptor antagonism, and adenosine A2A receptor antagonism. Due to the aforesaid pharmacodynamics, when ingested, most individuals report opioidergic and/or stimulatory effects.

CBs are a group of chemicals known to activate CB receptors in cells. These chemicals, which are found in cannabis plants, are also produced endogenously in humans and other animals, these are termed endocannabinoids. There are also synthetic CBs that are chemicals with similar structures to plant CBs or endocannabinoids. Plant cannabinoids can also be isolated such that they are "essentially pure" compounds. These isolated CBs are largely free of other naturally occurring compounds, such as other minor CBs and molecules.

The primary CB receptor subtypes are CB receptors type 1 (CB1) and type 2 (CB2). CB1 receptors are highly expressed in the Central Nervous System (CNS), especially the basal ganglia, and also identified in almost all peripheral tissues and cell types. CB2 receptors are expressed primarily in the immune system, where they modulate inflammation, but are also expressed in the CNS, particularly in neurons within the dorsal vagal motor nucleus, the nucleus ambiguous, the spinal trigeminal nucleus, and microglia. CB2 receptors were also found in the basal ganglia and studies suggest that impairment of these receptors may be associated with dyskinesia. While most actions of CBs are related to CB1 and CB2 receptors, other receptor types have been described, including the Transient Receptor Potential Vanilloid type 1 (TRPV1) cation channel, the GTP-binding Protein-coupled Receptor GPR55, the abnormal-CBD receptor, and the Peroxisome-Proliferator-Activated Receptor (PPAR).

Endogenously produced CBs (eCBs) are lipophilic compounds that demonstrate varying degrees of affinity for G-protein coupled CB receptors and include anandamide and 2-arachidonoglycerol. eCBs primarily function through retrograde signaling, wherein post-synaptic activity leads to eCB production and release with backward transmission across the synapse to depress presynaptic neurotransmitter release. The Endo-Cannabinoid System (ECS) may also support synapse formation and neurogenesis. Within the basal ganglia, eCBs and CB1 receptors tend to increase GABAergic and inhibit glutamatergic transmission. eCBs also tend to inhibit dopamine release through GABAergic mechanisms. eCBs are not stored and are quickly degraded after exerting a transient and localized effect. Removal of eCBs from the extracellular space occurs through cellular uptake and metabolism with anandamide degraded primarily by Fatty Acid Amide Hydrolysis (FAAH) and 2-AG degraded by monoacylglycerol lipase.

The disclosed invention finds that, in one embodiment, a number of alkaloids contained in *Mitragyna speciosa* and *Cannabis sativa* plants, when combined, could be used as a substitute for morphine, having a potent analgesic action, and can provide a sedative and muscle relaxant effects akin to the effects of benzodiazepines. Mitragynine and 7-hydroxymitragynine, found in *Mitragyna speciosa*, as well as tetrahydrocannabinol (THC) and cannabidiol (CBD), found in *Cannabis sativa*, are the two groups of alkaloids mainly responsible for the analgesic and muscle relaxant effects. Mitragynine and 7-hydroxymitragynine are partial agonists of the μ-subtype opioid receptor (MOR) (Kruegel, et al., 2016). In mice, 7-hydroxymitragynine was thirteen times more potent analgesic than morphine even upon oral administration (Matsumoto, et al., 2004). The effect of Kratom alkaloids as opioid receptor agonist is confirmed by the fact that it is readily antagonized by the opioid receptor antagonist naloxone (Yamamoto, et al., 1999). In addition, 5-HT2a and postsynaptic α2-adrenergic receptors, as well as neuronal $Ca^{2+}$ channels are also involved in the unique pharmacological and behavioral activity of mitragynine.

In addition, mitragynine exhibits antinociceptive and cough-suppressant effects that are comparable to those of codeine in animal studies (Macko, Weisbach, & Douglas, 1972). It has been reported that a methanol extract of Kratom leaf and a major alkaloid, mitragynine, produced skeletal muscle relaxation. Thus, mitragynine also has a direct effect on skeletal muscle by decreasing the muscle twitch. More so, Chittrakarn et al. (2010), report that Kratom extract had a greater effect at the neuromuscular junction than on the skeletal muscle or somatic nerve.

With CBs, likewise, a number of clinical trials in humans demonstrated that CBs might be useful in the treatment of movement disorders and pain. It has been suggested that an endogenous CBs participate in the control of movements and, therefore, the central ECS might play a role in the pathophysiology of these diseases. There is also evidence that CBs are of therapeutic value in the treatment of tics in Tourette Syndrome (TS), the reduction of Levodopa-Induced Dyskinesia (LID) in PD and some forms of tremor and dystonia. There is also evidence that CBs are useful in the treatment of chorea in HD and hypokinetic parkinsonian syndromes. Currently, treatments of these and similar diseases are focused on relieving symptoms and preventing complications because there is no curative therapy. Preclinical research in animal models of several movement disorders have shown variable evidence for symptomatic benefits but more consistently suggest potential neuroprotective effects in several animal models of PD and HD. Clinical observations and clinical trials of CB-based therapies suggest a possible benefit of CBs for tics.

Kratom extract contains multiple alkaloids, where some of them have therapeutic potential. The following activity effects and concentrations are compiled from several studies of alkaloids and their concentrations in *Mitragyna speciosa*. Results of one of the studies is presented in FIG. 2. The following list, though, is not inclusive and the alkaloids shall be further studied to determine their activity: ajmalicine (raubasine)—cerebrocirculant, antiaggregant, anti-adrenergic (at alpha-1), sedative, anticonvulsant, smooth muscle relaxer (found in Rauwolfia serpentine); ciliaphylline—antitussive, analgesic <1% of total alkaloid content found in Kratom leaf; corynantheidine—μ-opioid antagonist (also found in Yohimbe)<1% of total alkaloid content found in Kratom leaf; corynoxeine—calcium channel blocker <1% of total alkaloid content found in Kratom leaf; corynoxine—dopamine mediating anti-locomotives <1% of total alkaloid content found in Kratom leaf; epicatechin—antioxidant, antiaggregant, antibacterial, antidiabetic, antihepatitic, anti-inflammatory, anti-leukemic, antimutagenic, antiperoxidant, antiviral, potential cancer preventative, alpha-amylase inhibitor (also found in dark chocolate); 9-hydroxycorynantheidine—partial opioid agonist; 7-hydroxymitragynine—analgesic, antitussive, antidiarrheal; primary psychoactive in Kratom, approximately 2% of total alkaloid content found in Kratom leaf; isomitraphylline—immune-stimulant, anti-leukemic <1% of total alkaloid content found in Kratom leaf; isomitrafoline <1% of total alkaloid content found in Kratom leaf; isopteropodine—immuno-stimulant; isorhynchophylline—immuno-stimulant <1% of total alkaloid content found in Kratom leaf; isospeciofoline: <1% of total alkaloid content found in Kratom leaf; mitraciliatine <1% of total alkaloid content found in Kratom leaf; mitragynine—indole alkaloid, analgesic, antitussive, antidiarrheal, adrenergic, antimalarial, possible psychedelic (5-HT2A) antagonist, approximately 66% of total alkaloid content found in Kratom leaf; mitragynine oxindole B<1% of total alkaloid content found in Kratom leaf; mitrafoline <1% of total alkaloid content found in Kratom leaf; mitraphylline—oxindole alkaloid, vasodilator, antihypertensive, muscle relaxer, diuretic, antiamnesic, anti-leukemic, possible immunostimulant <1% of total alkaloid contents in Kratom leaf; paynantheine—indole alkaloid, smooth muscle relaxer, 8.6% to 9% of total alkaloid contents in Kratom leaf; rhynchophylline—vasodilator, antihypertensive, calcium channel blocker, antiaggregant, anti-inflammatory, antipyretic, anti-arrhythmic, antithelmintic <1% of total alkaloid content found in Kratom leaf; speciociliatine—weak opioid agonist, 0.8% to 1% of total alkaloid content of Kratom leaf, unique to Kratom; speciogynine—smooth muscle relaxer, 6.6% to 7% of total alkaloid contents of Kratom leaf; speciophylline—indole alkaloid, anti-leukemic <1% of total alkaloid contents of Kratom leaf; tetrahydroalstonine—hypoglycemic, anti-adrenergic (at alpha-2).

As in all botanicals, *Mitragyna speciosa* and *Cannabis sativa* alkaloid content varies quantitatively from geographical location, and from month to month, at different leaf harvest times. This led some teams to conclude that there may be different geographical variants within the same species. The Chelsea College Pharmacognosy Research Laboratories collected thirty samples of Kratom from Thailand, Malaysia, and Papua New Guinea between 1961 and 1970. All contained mitragynine, but also proved to have considerable variation in the alkaloid makeup. For red and green/white leaved plants of Thailand, the most common alkaloidal profile was mitragynine, speciogynine, speciociliatine, paynantheine, traces of ajmalicine, traces of (C9) methoxy-oxindoles, and traces of other indoles.

Yet other Thai plants contained distinct alkaloidal profiles, some with many more alkaloids. In the Malay specimens, one contained mitragynine, speciofoline, and other indoles and oxindoles, while others contained mitragynine, ajmalicine, speciogynine, speciociliatine, paynantheine, traces of indoles, and (C9) methoxy-oxindoles. Specimens from Papua New Guinea contained mitragynine, speciogynine, speciociliatine, paynantheine, specionoxeine, and isospecionoxeine. Other researchers reported that Thai and Malay Kratom had the alkaloids mitragynine, speciogynine, speciociliatine, paynantheine and 7-hydroxymitragynine in common.

In both Thai and Malay samples, mitragynine was the most abundant alkaloid, yet it made up 66% of the total alkaloid in the Thai Kratom sample, while it made up only 12% of the alkaloids from the Malaysian sample. The Malay Kratom sample had mitragynaline and pinoresinol as major components, as well as mitralactonal, mitrasulgynine and 3,4,5,6-tetradehydromitragynine. In the Malay Kratom, 4 new types of indole alkaloids (corynantheidaline, corynantheidalinic acid, mitragynaline and mitragynalinic acid) were discovered in very young leaves.

Likewise, *Cannabis sativa* alkaloid content and yield also depends on the plant type (drug, fiber), pollination, sex, age, part of the plant, cultivation (indoor, outdoor etc.), harvest time and conditions, drying, as well as storage. From 1980 to 1997, a total of 35,213 samples of confiscated Cannabis products (Cannabis, hashish, hashish oil) representing more than 7717 tons seized in the United States were analyzed by gas chromatography (GC). The mean THC concentration increased from less than 1.5% in 1980 to 4.2% in 1997. The maximum levels found were 29.9 and 33.1% in marijuana and sinsemilla Cannabis, respectively, where the highest THC concentrations measured were 52.9 and 47.0%, respectively. Concentration of THC in marijuana has lately increased significantly due to the progress in breeding, the tendency to cultivate under indoor conditions, and the worldwide access to and exchange of seeds originating from high-THC cultivars via the Internet. However, this is not the case when it comes to CBD, it is rare to find such high numbers. Any CBD content level that is 4% or higher is considered a high CBD strain. Strains with up 18% CBD have emerged in the last several years, but commercially available high CBD strains contain on average between 8-12% CBD.

The *Cannabis sativa* plant and its products consist of many chemicals. Some of the 483+ compounds identified are unique to Cannabis, for example, more than 60 cannabinoids, whereas the terpenes, with about 140 members forming the most abundant class. So far, 66 cannabinoids have been identified, and they are divided into 10 subclasses: 1) Cannabigerol class: cannabigerolic acid (CBGA)—antibiotic; cannabigerolic acid monomethylether (CBGAM); cannabigerol (CBG)—antibiotic, antifungal, anti-inflammatory, relaxant (possibly inhibits the uptake of GABA); cannabigerol monomethylether (CBGM); cannabigerovarinic acid (CBGVA); cannabigerovarin (CBGV); 2) Cannabichromene class: cannabichromenic acid (CBCA); cannabichromene (CBC)—anti-inflammatory, antibiotic, antifungal, analgesic; cannabichromevarinic acid (CBCVA); cannabichromevarin (CBCV); 3) Cannabidiol class: cannabidiolic acid (CBDA)—antibiotic; cannabidiol (CBD)—anxiolytic, antipsychotic, analgesic, anti-inflammatory, antioxidant, antispasmodic; cannabidiol monomethylether (CBDM); cannabidiol-C4 (CBD-C4); cannabidivarinic acid (CBDVA); cannabidivarin (CBDV); cannabidiorcol (CBD-C1); 4) Delta-9-tetrahydrocannabinol class: delta-9-tetrahydrocannabinolic acid A (THCA-A), delta-9-tetrahydrocannabinolic acid B (THCA-B), delta-9-tetrahydrocannabinol (THC)—euphoric analgesic, anti-inflammatory, antioxidant, antiemetic; delta-9-tetrahydrocannabinolic acid-C4 (THCA-C4), delta-9-tetrahydrocannabinol-C4 (THC-C4); delta-9-tetrahydrocannabivarinic acid (THCVA); delta-9-tetrahydrocannabivarin (THCV)—analgesic, euphoriant; delta-9-tetrahydrocannabiorcolic acid (THCA-C1); delta-9-tetrahydrocannabiorcol (THC-C1); delta-7-cis-iso-tetrahydrocannabivarin; 5) Delta-8-tetrahydrocannabinol class: delta-8-tetrahydrocannabinolic acid ($\Delta^8$-THCA); delta-8-tetrahydrocannabinol ($\Delta^8$-THC)—similar to THC (less potent); 6) Cannabicyclol class: cannabicyclic acid (CBLA); cannabicyclol (CBL); cannabicyclovarin (CBLV); 7) Cannabielsoin class: cannabielsoic acid A (CBEA-A); cannabielsoic acid B (CBEA-B); cannabielsoin (CBE); cannabinol (CBN)—sedative, antibiotic, anticonvulsant, anti-inflammatory; cannabinol methylether (CBNM); cannabinol-C4 (CBN-C4); cannabivarin (CBV); cannabinol-C2 (CBN-C2); cannabiorcol (CBN-C1); cannabinadiol (CBND); cannabinodivarin (CBVD); 8) Cannabitriol class: cannabitriol (CBT); 10-ethoxy-9-hydroxy-delta-6a-tetrahydrocannabinol; 8,9-dihydroxy-delta-6a-tetrahydrocannabinol; cannabitriolvarin (CBTV); ethoxy-cannabitriolvarin (CBTVE); 8) Miscellaneous cannabinoids class: dehydrocannabifuran (DCBF); cannabifuran (CBF); cannabichromanon (CBCN); cannabicitran (CBT); 10-oxy-delta-6a-tetrahydrocannabinol (OTHC); delta-9-cis-tetrahydrocannabinol (cis-THC); 3,4,5,6-tetrahydro-7-hydroxy-alpha-alpha-2-trimethyl-9-n-propyl-2,6-methano-2H-1-benzoxocin-5-methanol (OH-iso-HHCV); cannabiripsol (CBR); trihydroxy-delta-9-tetrahydrocannabinol (triOH-THC).

The typical scent of Cannabis results from about 140 different terpenoids—isoprene units (C5H8) form monoterpenoids (C10 skeleton), sesquiterpenoids (C15), diterpenoids (C20), and triterpenoids (C30). Terpenoids may be acyclic, monocyclic, or polycyclic hydrocarbons with substitution patterns including alcohols, ethers, aldehydes, ketones, and esters.

The essential oil (volatile oil) from *Cannabis sativa* can easily be obtained by steam distillation, vaporization, or other extraction methods. As already mentioned, the yield depends on the plant type, pollination, sex, age, part of the plant, cultivation (indoor, outdoor etc.), harvest time, drying, storage, etc. For example, fresh buds from an Afghani variety yielded 0.29% essential oil; where drying and storage reduced the content from 0.29% after 1 week and 3 months to 0.20% and 0.13%, respectively. Monoterpenes showed a significantly greater loss than sesquiterpenes, but none of the major components completely disappeared in the drying process. About 1.3 L of essential oil per ton, resulted from freshly harvested outdoor-grown *Cannabis sativa*, corresponding to about 10 L/ha.

The yield of nonpollinated (sinsemilla) plant at 18 L/ha was more than twofold compared with pollinated (8 L/ha). Sixty-eight components were detected by GC and GC/mass spectrometry in fresh bud oil distilled from high-potency, indoor-grown *Cannabis sativa*. Further, 57 constituents have been identified, where 92% were monoterpenes, 7% sesquiterpenes, and approximately 1% were other compounds. The dominating monoterpenes were myrcene (67%) and limonene (16%). In the essential oil from outdoor-grown *Cannabis sativa*, the monoterpene concentration varied between 47.9 and 92.1% of the total terpenoid content, and the sesquiterpenes ranged from 5.2 to 48.6%. The most abundant monoterpene was E-myrcene, followed by transcaryophyllene, D-pinene, trans-ocimene, and D-terpinolene. "Drug-type" Cannabis plant generally contained less caryophyllene oxide than "fiber-type," but even in "drug-type," the THC content of the essential oil was not more than 0.08%.

The 50 known hydrocarbons detected in Cannabis sativa consist of n-alkanes ranging from C9 to C39, 2-methyl-, 3-methyl-, and some dimethyl alkanes. Cannabis sativa L. is one of the rare psychotropic plants in which the central nervous system activity is not linked to particular alkaloids. However, two spermidine-type alkaloids (cannabisativine and anhydrocannabisativine) have been identified among more than 70 nitrogen-containing constituents, and five lignanamide derivatives have been isolated, including cannabisin A, B, C, and D. Besides, twelve simple amines, including piperidine, hordenine, methylamine, ethylamine, and pyrrolidine, are present in Cannabies; three proteins: edestin, zeatin, and zeatinnucleoside; six enzymes: edestinase, glucosidase, polyphenoloxydase, peptidase, peroxidase, and adenosine-5-phosphatase; and 18 amino acids that are of a common structure for plants.

Thirteen monosacharides (fructose, galactose, arabinose, glucose, mannose, rhamnose, etc.), two disaccharides (sucrose, maltose), and five polysaccharides (raffinose, cellulose, hemicellulose, pectin, xylan) have been identified so far. In addition, 12 sugar alcohols and cyclitols (mannitol, sorbitol, glycerol, inositol, quebrachitol, etc.) and two amino sugars (galactosamine, glucosamine) were found; as well as twenty-three commonly occurring flavonoids have been identified in Cannabis plant, existing mainly as C-/O- and O-glycosides of the flavon- and flavonol-type aglycones apigenin, luteolin, quercetin, and kaempferol. Thirty-four noncannabinoid phenols are known to be present in Cannabis plant: nine with spiro-indan-type structure (e.g., cannabispiran, isocannabispiran), nine dihydrostilbenes (e.g., cannabistilbene I, -II), three dihydrophenanthrenes (e.g., cannithrene-1, -2), and six phenols, phenol methylethers, and phenolic glycosides. Seven alcohols (e.g., methanol, ethanol, 1-octene-3-ol), 12 aldehydes (e.g., acetaldehyde, isobutyraldehyde, pentanal), 13 ketones (e.g., acetone, heptanone-2, 2-methyl-2-heptene-6-one), and 21 acids (e.g., arabinic acid, azealic acid, gluconic acid) have also been identified. Cannabis also contains phytosterols: campesterol, ergosterol, E-sitosterol, and stigmasterol, as well as vitamin K, which is the only vitamin found in Cannabis, whereas carotene and xanthophylls are reported pigments; and 18 elements were detected as well (e.g., Na, K, Ca, Mg, Fe, Cu, Mn, Zn, Hg).

Prior to the late 1990's, nearly all chemical studies of Kratom activity focused on mitragynine with the assumption that mitragynine was the main active alkaloid in Mitragyna speciosa. With 7-hydroxymitragynine now clearly identified as the principal psychoactive alkaloid in Kratom, many elements of these studies must be revised. The variety of alkaloids discovered in diverse Kratom samples to date, still calls for further studies and experimentation, investigating their specific activity, effects and potential applications. Through its makeup and tradition of use, it is clear Mitragyna speciosa is much more than a simple opioid-like narcotic and mild stimulant. Many of the secondary chemicals found in Mitragyna speciosa are present in small yet appreciable quantities, and their synergetic role and activity in the general pharmacology of Mitragyna speciosa is not yet fully understood. Nonetheless, Kratom provides an opportunity for researchers and pharmaceutical industry to develop new medicines that are potentially safer and more effective. And even more so, when certain Kratom alkaloids are combined with cannabis the pharmacological effect is amplified.

One embodiment of this invention proposes several potentially more safe and effective compounds of Mitragyna speciosa and Cannabis sativa alkaloids that are extracted, purified and combined to provide a pharmaceutical-grade compound for treatment of pain and other symptoms associated with diseases, disorders, medical conditions, and having other applications that are contemplated by this invention. Another embodiment of this invention provides an effective drug delivery system that allows timed release of the active ingredients necessary to achieve high efficacy with minimum side effects. Another embodiment of this invention describes methodologies for effective treatment of patients having the medical and other conditions contemplated by this invention.

As already mentioned, Mitragyna speciosa contains certain alkaloids, such as the 7-hydroxymitragynine and mitragynine that reportedly exhibit more potent analgesic actions than that of morphine and having reduced side effects, most importantly—significantly reduced respiratory depression and lesser addiction liability due to the presence of kappa-opioid receptor antagonists (Kruegel, et al., 2016), relatively analogous in mechanism of action to the drug buprenorphine. The multiple receptor targets are beneficial in the treatment of pain, and especially complex pain syndromes, such as the neuropathic pain. But unlike the buprenorphine, in some embodiments, when certain Kratom alkaloids are combined with cannabinoids, such as THC, the proposed compound provides vasodilating, antihypertensive, muscle relaxing, immune-stimulating, anti-inflammatory, antipyretic, anti-arrhythmic, antitussive, and mild adrenergic effects, where the mild stimulating effect of mitragynine (in low doses) and THC helps to reduce drowsiness associated with higher doses of opioids or opioid-like substances.

Despite the addiction and other concerns, morphine and its derivatives remain to be the primary medicines to treat severe pain. Cannabis-based medicines are also now being offered for treatment of muscle spasticity in patients with MS. For example, Sativex—a CB extract oral spray containing THC and CBD—is known to relieve many MS symptoms. Sativex and other CB-based medicines can be used to treat neuropathic pain, nausea associated with cancer chemotherapy, as well as stimulate appetite in HIV patients. Nevertheless, morphine remains to be the indispensable analgesic for improving patients' quality of life (QOL) in the cases of cancer and other illnesses causing severe pain. However, morphine has problems of, for example, having low bioavailability and causing various side effects, such as formation of analgesic resistance and physical or psychological dependence due to continued use, nausea and vomiting, constipation, sleepiness, and most importantly respiratory depression.

With that said, the advent of a potent and more safe analgesic, serving as a substitute for morphine, has long been needed. In search of such analgesics, investigations of synthetic analogs were performed with chemical modification of a morphine molecule, starting the 1920s and until the present day. Many compounds were synthesized since then and evaluated. However, there are not many examples of an opioid analgesic substance that is as effective as morphine or its synthetic analogs but safer than them. Current research has focused on an analgesic action of morphine and efforts are currently made to elucidate a molecular mechanism of analgesia on the basis of, for example, classification of opioid receptors (δ-, μ- and κ-receptors) and determination of amino acid sequences thereof. However, there are complicated interactions among those three kinds of receptors, and a logical methodology for separating an analgesic property from side effects, such as a narcotic property, has not been established to date.

Several other opioid pharmaceutical products exist which provide analgesic relief but at the same time may have fewer side effects and lesser addiction liability. For example, buprenorphine, sold under the brand name Subutex, among others, is an opioid used to treat opioid addiction, acute pain, and chronic pain. It comes in injectable, transdermal, sublingual, and other dosage forms. Maximum pain relief is generally achieved within an hour with effects lasting up to 24 hours. Buprenorphine affects different types of opioid receptors in different ways. In simplified terms, buprenorphine can essentially be thought of as a non-selective, mixed agonist—antagonist opioid receptor modulator, acting as a weak partial agonist of the MOR, an antagonist of the KOR, an antagonist of the DOR, and a relatively low-affinity, very weak partial agonist of the ORL-1. Full analgesic efficacy of buprenorphine requires both exon 11 and exon 1-associated μ-opioid receptor splice variants. Side effects may include respiratory depression, sleepiness, adrenal insufficiency, QT prolongation, low blood pressure, allergic reactions, and opioid addiction. Among those with a history of seizures, there is a risk of further seizures. Opioid withdrawal following stopping is generally mild.

Tramadol is another opioid pharmaceutical product that provides analgesic relief but has fewer side effects and reduced addiction liability. Tramadol is sold under the brand name Ultram, among others, and it is an opioid pain medication used to treat moderate to moderately severe pain. When taken by mouth in an immediate-release formulation, the onset of pain relief usually occurs within an hour. It is often combined with paracetamol (acetaminophen) as this is known to improve the efficacy of tramadol in relieving pain. It works by binding to the μ-opioid receptor and as a serotonin-norepinephrine reuptake inhibitor (SNRT). Tramadol is in the benzenoid class, and in the body, it is converted to desmetramadol, which is a more potent opioid. Common side effects include: constipation, itchiness and nausea. Serious side effects may include seizures, increased risk of serotonin syndrome, decreased alertness, and drug addiction. Long-term use of high doses of tramadol will cause physical dependence and withdrawal syndrome. Tramadol withdrawal typically lasts longer than that of codeine and other weak opioids (seven days or more of acute withdrawal symptoms). However, according to a 2014 report by the World Health Organizations Expert Committee on Drug Dependence, evidence of tramadol physical dependence was considered minimal. Consequently, tramadol is generally considered to be a drug with low potential for dependence.

There are a number of opioid receptor-modulating investigational analgesics that are currently under development for clinical use. For example: Axelopran/oxycodone—combination of a centrally active μ-opioid receptor agonist and a peripherally selective μ-, κ-, and δ-opioid receptor antagonist; Cebranopadol (GRT-6005)—non-selective μ-opioid receptor, nociceptin receptor, and δ-opioid receptor full agonist and κ-opioid receptor partial agonist; Desmetramadol (O-desmethyltramadol; Omnitram)—μ-opioid receptor agonist, norepinephrine reuptake inhibitor (NRI), and 5-HT2C receptor antagonist; Difelikefalin (CR845, FE-202845)—peripherally selective κ-opioid receptor agonist. Lexanopadol (GRT-6006, GRT13106G)—non-selective opioid receptor agonist; Nalbuphine sebacate (dinaphine, sebacoyl dinalbuphine ester; LT-1001)—long-lasting prodrug of nalbuphine, μ- and κ-opioid receptor partial agonist; NKTR-181-selective μ-opioid receptor full agonist that slowly enters the brain; Oliceridine (TRV130)—μ-opioid receptor biased agonist; Oxycodone/naltrexone—combination of a μ-opioid receptor agonist and a μ- and κ-opioid receptor antagonist, and others.

A study was undertaken to determine the analgesic and anti-inflammatory activity of various CBs and CB precursors. Oral administration of CBD was found to be the most effective at inhibition of phenyl-p-benzoquinone-induced writhing in mice. It was noted that with the exception of CBN and delta 1-THC, the cannabinoids and olivetol (their biosynthetic precursor) demonstrated activity in the PBQ test exhibiting their maximal effect at doses of about 100 micrograms/kg. Delta 1-THC only became maximally effective in doses of 10 mg/kg (this higher dose corresponded to that which induced catalepsy and is indicative of a central action). CNB demonstrated little activity and even at doses higher than 10 mg/kg could only produce a 40% inhibition of PBQ-induced writhing. And as mentioned earlier, CBD was the most effective of the cannabinoids at doses of 100 micrograms/kg. Doses of cannabinoids that were effective in the analgesic test orally were used topically to antagonize TPA-induced erythema of skin. Formukong et al. (1988) conclude that delta 1-THC and CBN were the least effective in this test, suggesting a structural relationship between analgesic activity and anti-inflammatory activity among the cannabinoids related to their peripheral actions and separate from the central effects of delta 1-THC.

Thus, considering the many therapeutic effects, and specifically the analgesic effect of compounds containing CBs, particularly CBD and $(-)$-$\Delta^9$-trans-THC, there is a continuing need for improving existing CB-containing products as well as a need for new products and delivery systems containing CBs, especially in the pharmaceutical field.

Recent methods have also sought to find new ways to deliver CBs to a patient including those which bypass the stomach and the associated first pass effect of the liver which can remove up to 90% of the active ingested dose and avoid the patient having to inhale unhealthy tars and associated carcinogens into their lungs. Such dosage forms include administering the CBs to the sublingual or buccal mucosae, inhalation of a CB vapor by vaporization or nebulization, enemas or solid dosage forms such as gels, capsules, tablets, pastilles and lozenges.

To attain the required purity of isolated CBs and Kratom alkaloids, up to at least 97% by total weight, consistent ratio of CBs and Kratom alkaloids in the formulation, attain pharmaceutical-grade stability of active CBs and Kratom alkaloids, effective and consistent delivery system for treating multiple conditions, as well as therapeutically-effective treatment methods—requires a know-how that is proposed in this document.

As already mentioned, one objective of this invention is to provide a compound that has a potent analgesic action, which may serve as a substitute for morphine—a pharmaceutical composition and a treatment method. The novel compositions and treatment methods, with several variations, some of which are exemplified herein, exhibit a potent analgesic, anti-inflammatory, and muscle relaxing actions, and other actions contemplated by this invention. The proposed invention has relied on new scientific findings, experiments and anecdotal evidence obtained through this research. Inventors believe that this invention is unique and different from the existing art related to *Mitragyna speciosa*- based and *Cannabis sativa*-based compounds, processes, and methods. Some of the existing art is briefly outlined below.

The U.S. Pat. No. 7,968,594 referenced herein, discloses the invention that relates to treatment of cancer related pain and constipation. The subject in need is administered a combination of CBD and delta-9-THC in a predefined ratio by weight of approximately 1:1 of CBD to THC (U.S. Pat. No. 7,968,594, 2005).

The U.S. patent application Ser. No. 15/032,070 referenced herein, discloses a formula of compound containing 7-hydroxymitragynine that has an analgesic effect and high metabolic stability. The invention further provides the following: an analgesic obtained from the compound, a salt thereof, or solvates of the compound and salt; a pharmaceutical composition containing the compound, a salt thereof, or solvates of the compound and salt; an analgesic treatment method using the compound, a salt thereof, or solvates of the compound and salt; and a use of the compound, a salt thereof, or solvates of the compound and salt, in the production of an analgesic composition (U.S. Pat. No. 15,032,070, 2014).

The U.S. Pat. Application No. 20110245287 referenced herein, discloses hybrid opioid compounds, mixed opioid salts, compositions comprising the hybrid opioid compounds and mixed opioid salts, and methods of use thereof that among other substances may contain Kratom alkaloids. More particularly, in one aspect the hybrid opioid compound includes at least two opioid compounds that are covalently bonded to a linker moiety. In another aspect, the hybrid opioid compound relates to mixed opioid salts comprising at least two different opioid compounds or an opioid compound and a different active agent. Also disclosed are pharmaceutical compositions, as well as methods of treating pain in humans using the hybrid compounds and mixed opioid salts (U.S. Pat. No. 20,110,245,287, 2011).

The U.S. Pat. Ser. No. 13/024,298 referenced herein, discloses a compound that may contain Kratom alkaloids, being a pharmaceutically acceptable salt or ester thereof, and a method of treating a subject afflicted with pain, a depressive disorder, a mood disorder or an anxiety disorder by administering the compound to the subject (U.S. Pat. No. 13,024,298, 2011).

The U.S. Pat. Application No. 20060135599 referenced herein, discloses the invention that relates to the use of one or more CBs in the treatment of neuropathic or chronic pain. A method of treating brachial plexus avulsion in a human patient comprising administering to a patient in need thereof effective amount one or more CBs (U.S. Pat. No. 20,060,135,599, 2003).

SUMMARY OF THE INVENTION

The following description presents a simplified view of one or more aspects of the proposed invention. This summary is not an extensive overview of all the contemplated embodiments and implementations. It is intended to neither identify key or critical elements of all features, nor delineate the scope of any or all facets. Its sole purpose is to present some concepts of one or more aspects in a simplified form.

It was discovered, that the use of *Cannabis sativa* and *Mitragyna speciosa*-combined extracts in the ratio of approximately 1:1 by mass, or 1:2 by mass, or 2:1 by mass, or from 1:99 to 99:1 by mass, containing components that are extracted from plant material is more effective in the treatment of spasms, inflammation, and pain in subjects in need thereof than each extract alone.

It was also discovered that some unwanted side effects caused by currently available medications are reduced or eliminated by treatment with the compound disclosed herein, for example: Marinol in the case of MS, morphine in the case of cancer and trauma, tetrabenazine and benzodiazepine in the case of HD, and others.

In one embodiment, the proposed invention includes a *Mitragyna speciosa* plant extract that contains 7-hydroxymitragynine and mitragynine, as well as a *Cannabis sativa* plant extract containing THC and CBD. The respective ranges of THC and CBD, as well as 7-hydroxymitragynine and/or mitragynine, may vary according to the starting plant material and the extraction methodology used. The plants extracts may be obtained by various means of extraction from the plant material. Such means include but are not limited to: supercritical or subcritical extraction with $CO_2$, extraction with hot gas, and extraction with solvents.

In another embodiment, the proposed invention includes a *Mitragyna speciosa* plant extract that contains mitragynine and at least one pharmacologically inactive substance, and the extract further contains at least a trace amount of 7-hydroxymitragynine and/or pseudoindoxyl, as well as at least a trace amount of one or more CBs, as well as other alkaloids, which are co-extracted from the plant material. Their respective ranges may vary according to the starting plant material and the extraction methodology used.

In another embodiment, the proposed invention includes a synthesis of mitragynine, THC, and CBD, using one of the available techniques, In another embodiment, the proposed compound contains some synthesized mitragynine and at least one pharmacologically inactive substance, and the compound further contains at least a trace amount of synthesized or *Mitragyna speciosa*-extracted 7-hydroxymitragynine and/or pseudoindoxyl, as well as at least a trace amount of one other of plurality of synthesized or *Mitragyna speciosa*-extracted indole or oxindole alkaloids, as well as at least a trace amount of one or more *Cannabis sativa*-extracted or synthesized CBs. Their respective ranges may vary according to the desired clinical effect or the type of symptom relief anticipated.

Although mitragynine is the major alkaloid in the extract of *Mitragyna speciosa*, a more careful study indicates a more potent analgesic alkaloid, 7-hydroxymitragynine (or pseudoindoxyl (mitragynine pseudoindoxyl)—a rearrangement product of 7-hydroxymitragynine). The 7-hydroxymitragynine (or pseudoindoxyl) is present in the mature leaves of *Mitragyna speciosa* (from Thailand and other regions). In another embodiment, the proposed invention includes a synthesis of 7-hydroxymitragynine, where the hydroxyl derivative, for instance, could be obtained from the oxidation of mitragynine with iodobenzene diacetate. In another embodiment, the proposed compound contains synthesized 7-hydroxymitragynine and/or pseudoindoxyl and at least one pharmacologically inactive substance, and the compound further contains at least a trace amount of synthesized or *Mitragyna speciosa* plant-extracted mitragynine, as well as at least a trace amount of one other of plurality of synthesized or *Mitragyna speciosa*-extracted indole or oxindole alkaloids, as well as at least a trace amount of one or more *Cannabis sativa*-extracted or synthesized CBs. Their respective ranges may vary according to the desired clinical effect or the type of symptom relief desired.

Further, in one embodiment the compound contains at least a trace amount of at least one of: paynantheine, 3-isopaynantheine, rhynchophylline, mitraphylline, mitrafoline, mitragynine oxindole, mitraciliatine, isospeciofoline, isorhynchophylline, isopteropodine, isomitrafoline, isomitraphylline, 9-hydroxycorynantheidine, epicatechin, corynoxine, corynoxeine, corynantheidine, ciliaphylline, akuammine, ajmalicine, tetrahydroalstonine, stipulatine, speciophylline, speciophylline, speciofoline, or any combination thereof, or a natural or synthetic analogue thereof, and/or derivatives thereof.

And in another embodiment the compound contains at least a trace amount of at least one of: CBGA, CBGAM, CBG), CBGM, CBGVA, CBGV, CBCA, CBC, CBCVA, CBCV, CBDA, CBD, CBDM, CBD-C4, CBDVA, CBDV, CBD-C1, THCA-A, THCA-B, THC, THCA-C4, THC-C4, THCVA, THCV, THCA-C1, THC-C1, delta-7-cis-iso-tetrahydrocannabivarin, $\Delta^8$-THCA, $\Delta^8$-THC, CBLA, CBL, CBLV, CBEA-A, CBEA-B, CBE, CBN, CBNM, CBN-C4, CBV, CBN-C2, CBN-C1, CBND, CBVD, CBT, 10-ethoxy-9-hydroxy-delta-6a-tetrahydrocannabinol, 8,9-dihydroxy-delta-6a-tetrahydrocannabinol, CBTV, CBTVE, DCBF, CBF, CBCN, CBT, OTHC, cis-THC, OH-iso-HHCV, CBR, triOH-THC, or any combination thereof, or a natural or synthetic analogue thereof, and/or derivatives thereof.

Further, in another embodiment the compound comprising of 0.1% to 70% THC of the total compound by mass; and/or 0.1% to 70% CBD of the total compound by mass; and/or 0.1% to 70% CBG of the total compound by mass; and/or 0.1% to 5% ajmalicine of the total compound by mass; and/or 0.1% to 5% ciliaphylline of the total compound by mass; and/or 0.05% to 3% corynantheidine of the total compound by mass; and/or 0.05% to 3% corynoxine of the total compound by mass; and/or 0.1% to 20% epicatechin of the total compound by mass; and/or a trace amount to 5% hydroxycorynantheidine of the total compound by mass; and/or a trace amount to 90% 7-hydroxymitragynine and/or pseudoindoxyl of the total compound by mass; and/or 0.01% to 10% isomitraphylline and/or isopteropodine and/or sorhynchophylline, and/or isospeciofoline of the total compound by mass; and 10% to 90% mitragynine and/or mitragynine oxindole and/or mitrafoline and/or mitraphylline of the total compound by mass; and/or 0.1% to 20% paynantheine and/or rhynchophylline of the total compound by mass; and/or a trace amount to 3% speciociliatine and/or speciogynine and/or speciophylline of the total compound by mass; and/or at least a trace amount of one or more other of plurality of indole or oxindole alkaloids, and at least one pharmacologically inactive substance.

In one embodiment of the proposed invention, the treatment of an autoimmune disease involves giving to a patient in the morning by oral administration one soft-gel capsule of the compound containing a mixture of the following pharmacologically active substances: 40% of mitragynine of the total compound by mass, and 5% of 7-hydroxymitragynine and/or pseudoindoxyl of the total compound by mass, and 15% of THC of the total compound by mass, and 40% of CBD of the total compound by mass, and a number of pharmacologically inactive substances, such as stabilizers. Said capsule is a time-released capsule designed to release said mixture in the small intestine; and in another embodiment, in the stomach. The aforesaid compound and method in some subjects may reduce neurological pain and spasticity symptoms associated with, in one embodiment, MS, having minimal psychotropic effect. In another embodiment, said compound is administered in conjunction with a therapeutic dose of pancuronium to increase the compound efficacy; and in another embodiment with succinylcholine to achieve muscle relaxation in anesthesia or intensive care, and in another embodiment with benzodiazepine.

In another embodiment of the proposed invention, the treatment of acute cancer pain involves giving to a patient every 6 hours by oral administration one soft-gel capsule of the compound containing a mixture of the following active substances: 50% THC of the total compound by mass, and 50% of 7-hydroxymitragynine and/or pseudoindoxyl of the total compound by mass, and where said compound contains one or more other of plurality of indole or oxindole alkaloids and/or CBs, and a number of pharmacologically inactive substances, such as lipid carriers and stabilizers. Said capsule is an immediate release capsule designed to release said mixture in the small intestine; and in another embodiment, in the stomach. The aforesaid compound and method in some subjects may reduce acute pain associated with cancer, and in another embodiment, with a medical procedure.

In another embodiment of the proposed invention, an athlete's performance enhancing plan includes taking by oral administration 30 minutes before the exercise a nutraceutical supplement, one tablet of the compound containing a mixture of the following active substances: 30% of mitragynine of the total compound by mass, and less than 1% of 7-hydroxymitragynine and/or pseudoindoxyl of the total compound by mass, and 4% epicatechin of the total compound by mass, but not more than 2 mg per kg of bodyweight, and 40% of CBD of the total compound by mass, and 25% ascorbic acid (C6H8O6) of the total compound by mass; and where said compound may contain one or more other of plurality of indole or oxindole alkaloids and a stabilizer. The aforesaid compound and method in some subjects may increase pain tolerance, increase physical and mental endurance, provide additional energy and elevate mental mood, as well as reduce physical and mental fatigue.

In another embodiment of the proposed invention, the treatment of inflammation involves giving to a patient 4 times in 24 hours by oral administration a dose of medicament, in one embodiment, a soft-gelatin capsule that consists of type A and/or B gelatin, water, and a plasticizer, such as glycerin or sorbitol; and encapsulates a compound containing a liquid mixture that includes: 40 mg of mitragynine, and no pseudoindoxyl and/or 7-hydroxymitragynine, and 40 mg of CBD, and 5 mg of THC, and citric acid, nanostructured lipid carrier system, and methyl and propyl parabens.

In another embodiment of the proposed invention, an athlete after an exercise is given a nutraceutical supplement that is a 355 ml carbonated drink that includes a mixture of 60 mg of mitragynine, and less than 1 mg of pseudoindoxyl and/or 7-hydroxymitragynine, as a product of natural mitragynine, oxidation, and 60 mg of *Cannabis sativa* extract that contains no or a trace amount of THC, and ascorbic acid (C6H8O6), and vitamin B complex, and sugar or sugar substitute, and preservatives, colorants, flavoring agents, and other ingredients. In another embodiment such nutraceutical supplement is a hard candy; and in another embodiment, it is an energy bar; and in another, a cereal; and in another, a sport nutrient mix.

The proposed invention provides methods and compounds for treatment of multiple diseases and disorders at various stages, and different patients potentially presenting different symptoms, and as such may require larger or smaller doses to achieve the desired efficacy. Besides, the different ratios of the *Cannabis sativa* and/or *Mitragyna speciosa* plant alkaloids, other ingredients are required to achieve the desired effect, such as proper absorption.

In one aspect of the invention, titration of doses is beneficial to patients as they can take smaller doses of the medication to achieve efficacy. It is understandable that not all patients will require the same dose of medication, for example, patients of a larger build or faster metabolism may require a higher dose than that required by a patient that is of a smaller build or slower metabolism. In one embodiment said titration is adjusted with a time-release and point of release-tailored dosage forms. For instance, a soft-gelatin capsule designed to release medication in doses in certain parts of the digestive system to achieve the desired efficacy.

In another embodiment, the dose of medicament to be administered to a subject suffering from chronic pain is formulated such that a specific patient can titrate such dose and not develop significant tolerance to the medication; where the term "titrate" means that the patient is provided with a medication that is in such a form or engineered in such a way that smaller doses than the unit dose can be taken. In one embodiment, the titratable dosage forms are gel, gel spray, transdermal patch, liquid, vapor, and the like.

The unit dosage—defined as a maximum dose of medication that can be taken at any one time or within a specified dosage period—may range, in one embodiment, between 5 mg and 1200 mg of said medicine for a patient that just starts using the medication, or, depending on the administration route and aforesaid variables, the dosage may fluctuate significantly, such that unit dosage may consist of multiple doses taken several times a day, especially for long-term use patients that have developed tolerance. Administration of the compound may be carried out by any of several suitable known means, including but not limited to intraperitoneal, subcutaneous, oral, intramuscular, intravenous, and other administration forms.

These and other embodiments and objects of the invention will become apparent upon further review of the specification and claims presented herein. Thus, the above and the following expressed embodiments and objects of the invention are not intended by the inventors to limit the scope of the invention.

BRIEF DESCRIPTION OF THE DRAWINGS

The accompanying drawings, which are incorporated in and constitute a part of this specification, illustrate aspects of the present teachings and together with the description, serve to explain principles of the present teachings.

The FIG. 1, incorporated herein by reference, shows, in one embodiment, isobolographic analysis of mitragynine (MIT) and THC combination in mice. The points A and B represent the $ED_{50}$ values for each drug. The line connecting these points contains dose pairs that are additive. The theoretical additive points for each drug combination are indicated on both graphs by C and D. The extrapolated experimental points for the combined substances are marked as E and F, and since they fall to the left and below the additivity line, they indicate the therapeutic synergism that is greater than the therapeutic effect of each substance combined.

The FIG. 2, incorporated herein by reference, provides one example of many possible *Mitragyna speciosa* alkaloid profiles and possible therapeutic effects of alkaloids. The depicted percentage is the estimated content in the alkaloid extracts (Hassana, et al., 2013).

Figure 3:
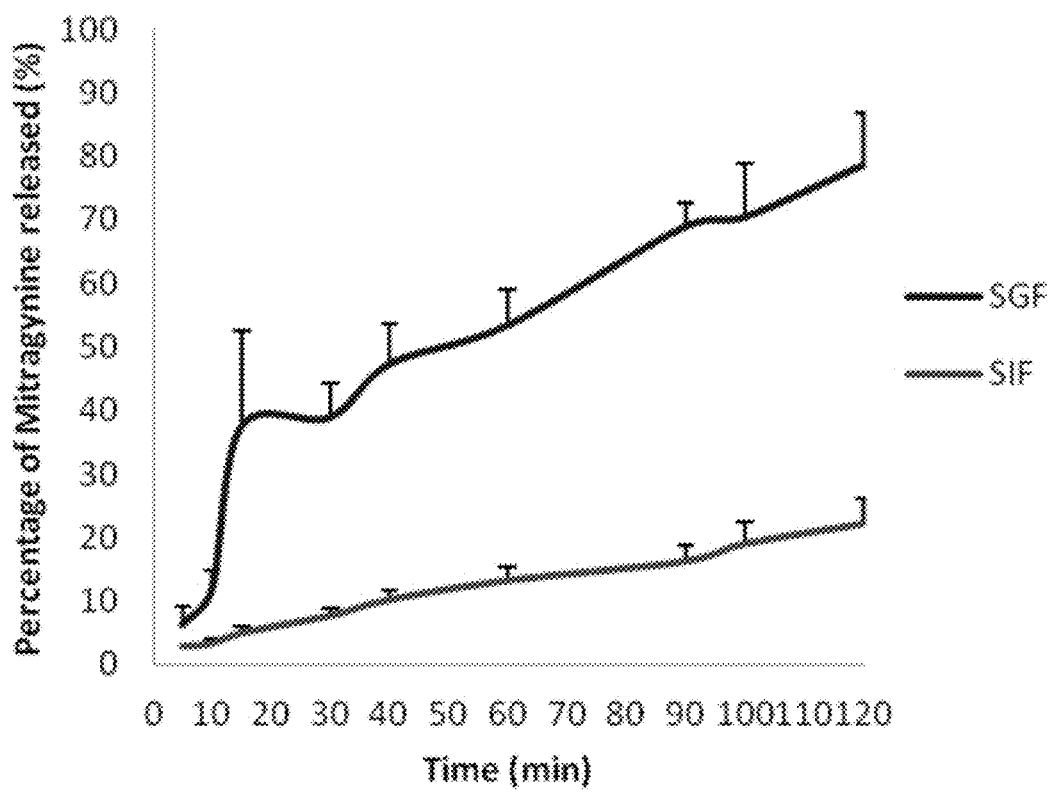

The FIG. 3, incorporated herein by reference, shows dissolution profiles of mitragynine in SIF and SGF (n=3) (Ramanathan, et al., 2015).

Figure 4:
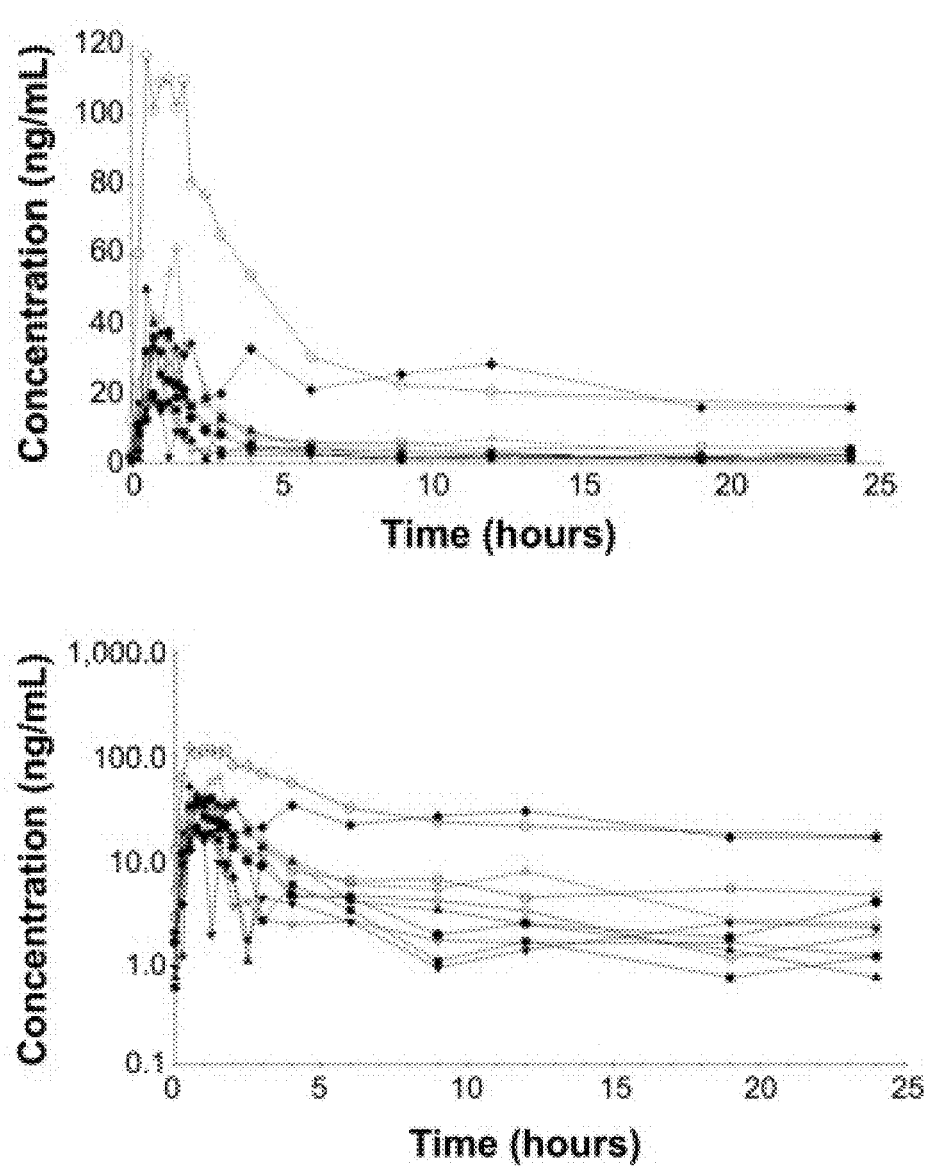

The FIG. 4, incorporated herein by reference, shows plasma mitragynine concentration—time curve of subjects after the administration of a loading dose: the normal plot (upper chart) and semi-logarithmic plot (lower chart) (Trakulsrichai, et al., 2015).

The FIG. 5, incorporated herein by reference, shows the chemical structure of mitragynine and its major analogues (Hassana, et al., 2013).

Figure 6:
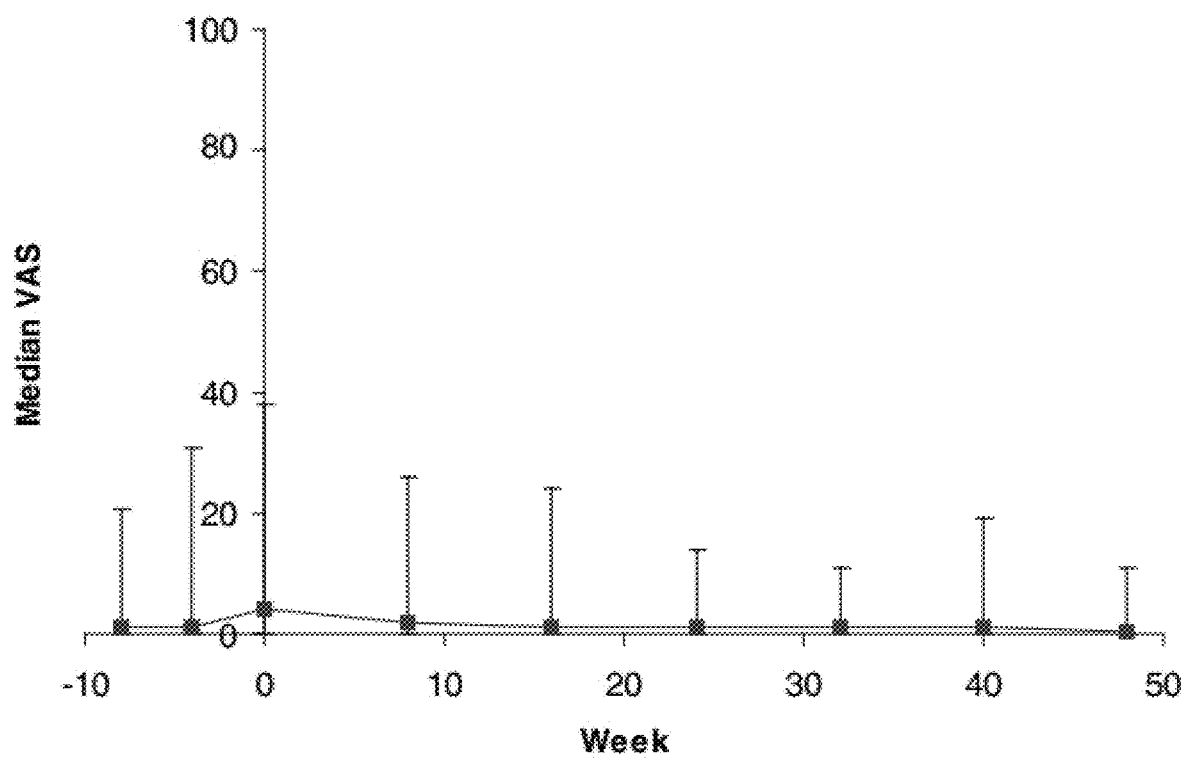

The FIG. 6, incorporated herein by reference, shows the long-term use toxicity of THC and CBD mixture (27 mg/mL and 25 mg/mL) in human patients. According to the study conducted by Wade et al., (2006) it represents the median intoxication scores (displaying the 10th and 90th percentiles which represents the central 80% of data) for 92 patients completing at least 48 weeks of treatment.

Figure 7:
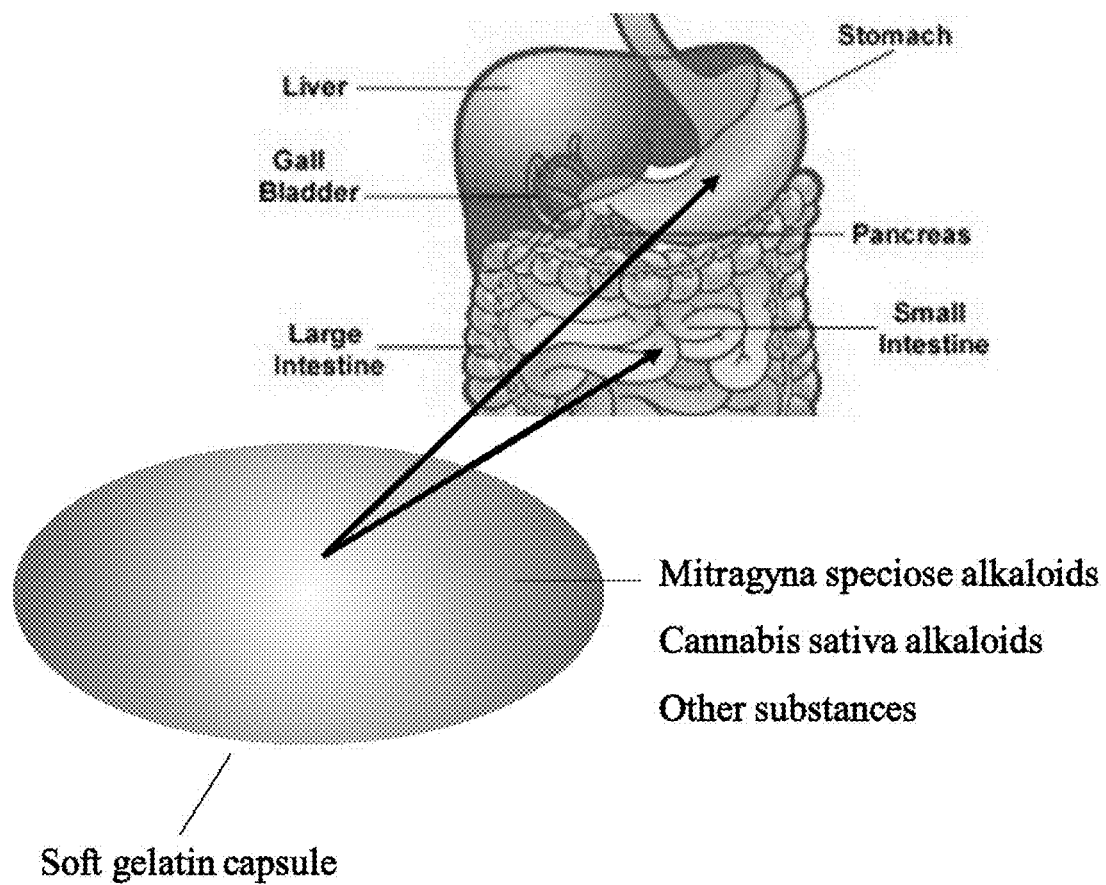

The FIG. 7, incorporated herein by reference, shows a variable-release soft-gelatin capsule pill, one of many possible dosage forms, that consists of predominantly type A or B gelatin, water, sorbitol, and encapsulates a compound containing a liquid mixture that includes: 100 mg of mitragynine, 10 mg of 7-hydroxymitragynine, 25 mg of CBD, 15 mg of THC, and lipid carrier, preservative, and less than 5% of other alkaloids and other substances.

DESCRIPTION OF EMBODIMENTS

Reference will now be made to embodiments, examples of which are illustrated in the accompanying material. In the following description, some details are set forth in order to provide understanding of the proposed invention. However, it will be apparent to one of ordinary skill in the art that the present invention may be practiced without these details. In other instances, well-known methods, procedures, components, circuits, and networks have not been described in detail so as not to unnecessarily obscure aspects of the embodiments.

It will also be understood that, although the terms first, second, etc., may be used herein to describe various elements, these elements should not be limited by these terms. These terms are only used to distinguish one element from another. For example, a first contact could be termed a second contact, and, similarly, a second contact could be termed a first contact, without departing from the scope of the present invention. The first contact and the second contact are both contacts, but they are not the same contact.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. Moreover, the term "or" is intended to mean an inclusive "or" rather than an exclusive "or." That is, unless specified otherwise, or clear from the context, the phrase "X employs A or B" is intended to mean any of the natural inclusive permutations. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if is detected" may be construed to mean "upon determining" or "in response to determining" or "upon detecting (the stated condition or event)" or "in response to detecting (the stated condition or event)," depending on the context.

As used herein, the terms "related", "in connection", or "associated", or "relevant", and similar, depending on the context, means any association, whether direct or indirect, by any applicable criteria as the case may be.

The word "exemplary" is used herein to mean "serving as an example, instance, or illustration". And no aspect of this disclosure shall be construed as preferred or advantageous over other aspects or designs unless expressly stated.

The term "cannabinoid(s)" represents cannabinoid receptor agonists and a group of C21 terpenophenolic compounds found in *Cannabis sativa* L, as well as synthetic or semi-synthetic cannabinoids, for instance, without limitation: nabilone, dexanabinol, ajulemic acid; and cannabinoid receptor ligands that are chemically different endocannabinoids, for instance, without limitation: anandamide; 2-arachidonoylglycerol; and other phytocannabinoids; levonantradol; CP 47,497; (C6)-CP 47,497; (C8)-CP 47,497; (C9)-CP 47,497; CP 50,556-1; CP 55,244; CP 55,940; CP-945,598; HHC; O-1871; AMG-36; AMG-41; AM-694; AM-906; AM-1235; AM-2232; AM-2233; AM-2389 O-1812; THJ-2201; JWH-018 and others.

The term "plant extract" is taken herein to refer to one or more plant extracts from any 7-hydroxymitragynine or mitragynine, or pseudoindoxyl, or CB-containing plants; it can also be understood as partially or fully synthesized or modified substances. In addition, the terms "cannabinoid-containing plant extract", or "cannabinoid extract", or "cannabis extract", or Cannabis plant, or similar are taken herein to refer to one or more plant extracts from any plant in the Cannabaceae family or any plant that contains any form of cannabinoid.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols; alkali or organic salts of acidic residues such as carboxylic acids. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkali metal salts, sodium, potassium or lithium.

As used herein, "treating" means preventing, slowing, halting, or reversing the progression of a disease or infection. Treating may also mean improving or attempting to improve one or more symptoms of a disease or infection.

As used herein, "trace amount" means as practiced in analytical chemistry—average concentration is less than 100 parts per million (ppm) measured in atomic count or less than 100 micrograms per gram.

The term "subject" or "patient" refers to a mammal in need of treatment or undergoing treatment using the inventive compounds described herein. Mammalian subjects include without limitation humans, dog, cat, horse or any other animal in need of treatment.

As used herein, the percent by mass of a mixture is obtained by dividing the mass of each component by the total mass and multiply by 100 (Percent by mass=mass of component/total mass×100%). For example. a mixture that contains 1.203 g CaCO3 and 1.797 g NaCl is equal to CaCO3=40.10% and NaCl=59.90%.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

The present invention provides treatment methods for reducing muscle spasms, inflammation, and treating pain associated with cancer, trauma, medical procedure, and neurological diseases and disorders in subjects in need thereof. The present invention further provides a number of pharmaceutical compounds that represent a stable, fast-acting formulation of naturally occurring alkaloids or their analogs (for the purpose of this document, may be used interchangeably). An analog herein refers to a compound that is derived by chemical, biological or synthetic transformation of the naturally occurring alkaloids of a *Mitragyna speciosa* and *Cannabis sativa* plants, or synthetically obtained similar compounds.

Illustrative of a *Mitragyna speciosa* plant alkaloids or their analogues are compounds selected from the group consisting of, and as further illustrated by FIG. 5, but not limited to: ajmalicine (raubasine), ciliaphylline, corynantheidine, corynoxeine, corynoxine, epicatechin, 9-hydroxy-corynantheidine, 7-hydroxymitragynine, isomitraphylline, isomitrafoline, isopteropodine, isorhynchophylline, isospeciofoline, mitragynine, mitragynine, mitrafoline, mitraphylline, paynantheine, rhynchophylline, speciociliatine, speciogynine, speciophylline, tetrahydroalstonine, a combination thereof, natural or synthetic analogues thereof, indole or oxindole alkaloids, and a natural or synthetic molecule with a basic similar structure.

Illustrative of a *Cannabis sativa* plant alkaloids are compounds selected from the group consisting of, but not limited to: CBGA, CBGAM, CBG), CBGM, CBGVA, CBGV, CBCA, CBC, CBCVA, CBCV, CBDA, CBD, CBDM, CBD-C4, CBDVA, CBDV, CBD-C1, THCA-A, THCA-B, THC, THCA-C4, THC-C4, THCVA, THCV, THCA-C1, THC-C1, delta-7-cis-iso-tetrahydrocannabivarin, $\Delta^8$-THCA, $\Delta^8$-THC, CBLA, CBL, CBLV, CBEA-A, CBEA-B, CBE, CBN, CBNM, CBN-C4, CBV, CBN-C2, CBN-C1, CBND, CBVD, CBT, 10-ethoxy-9-hydroxy-delta-6a-tetrahydrocannabinol, 8,9-dihydroxy-delta-6a-tetrahydrocannabinol, CBTV, CBTVE, DCBF, CBF, CBCN, CBT, OTHC, cis-THC, OH-iso-HHCV, CBR, triOH-THC.

The natural alkaloid compounds are readily obtained from plant tissue by suspending the tissue in an appropriate solvent to extract alkaloid compounds and other tissue components. Analytical purification of such an extract provides pharmaceutical grade alkaloid compounds. In one instance, mitragynine was found to be a pure compound upon spectroscopic analysis (including 1H and 13C NMR, IR, and mass spectrometry), and identified to be mitragynine by comparing the obtained spectra data with the published data.

Chittrakarn, et al. (2010), had performed said extraction and isolation of Kratom leaves red vein type. They were collected from Satoon province, in the southern part of Thailand during the months of February-May 2005. Air-dried leaves were pulverized by grinding and then macerated, at room temperature, with absolute methanol for 7 days, twice, while stirring 2-3 times/day. The extracts were mixed, filtered and concentrated using a rotary evaporator (BUCHI, B 169 Vacumn-System, Switzerland). Then they were freeze-dried (Corrosion Resistant Freezer Drier, FTS System, Inc., USA). The yield was 7.92% (w/w).

According to Chittrakarn, et al., (2010), said isolation of dried product from the methanolic extract of Kratom leaves was dissolved in 10% acetic acid solution. This solution was shaken and left overnight. The acidic filtrate was washed with petroleum ether, adjusted to pH 9 with 25% ammonia solution, and then extracted with chloroform. The chloroform extract was washed with distilled water, dried over anhydrous sodium sulfate and evaporated to yield a dry crude alkaloid extract. According to the isolation procedure, Chittrakarn, et al., (2010) report that the yield of crude alkaloid extract was approximately 0.25% based on fresh weight of *Mitragyna speciosa*. An aliquot (2.5 g) was then subjected to silica gel column chromatography, eluted with 5% methanol in chloroform to obtain a major alkaloid (1.25 g), which appeared as a single spot on TLC analysis (four different solvent systems). Overall, the yield of mitragynine in the methanolic extract was approximately 1.56%.

Alternatively, *Mitragyna speciosa* plant substances can be extracted from the plant tissue under supercritical conditions. Solvents used for supercritical extraction of alkaloids and other substances include without limitation: carbon dioxide, or other gases in isolation or combination with or without solvent modifiers, selected from ethanol, propanol, butanol, hexane, chloroform, dichloromethane, acetone, or any organic solvent capable of extracting such substances, and alcohol-water mixtures, for instance, water-ethanol or water-butanol mixtures, and others.

The present invention, in one embodiment, involves producing an extract from *Mitragyna speciosa* plant matter, containing mitragynine, pseudoindoxyl, and/or 7-hydroxymitragynine. In one embodiment, the dried plant matter is ground and subjected to a CO2 extraction and the primary extract obtained is separated. Specifically, ground *Mitragyna speciosa* plant material is compressed and charged into an extraction vessel. CO2 is then introduced, having been brought to a temperature, in one embodiment, of approximately 60° C. and to a pressure of approximately 250 bars. When the CO2 enters into contact with the material to be extracted, it extracts the desired components, in particular comprising mitragynine, pseudoindoxyl and/or 7-hydroxymitragynine, as well as other indole or oxindole alkaloids. In one embodiment, the extraction method permits extracting various isomers of alkaloids, selectively obtained from industrial *Mitragyna speciosa* plant, also separating undesirable, alkaloids, waxes and removing the solvent.

It is preferable, in one embodiment, that the extraction/production method yields substantially the mitragynine and 7-hydroxymitragynine that are believed to be the most effective alkaloids for pain management. There are also various other techniques that are known for extracting and isolating mitragynine and 7-hydroxymitragynine from *Mitragyna speciosa* plant. For example, Pat. No. CN 102,048,857 B, describes a method for extracting alkaloids from Kratom.

The natural CB compounds are also readily obtained from plant tissue by suspending the tissue in an appropriate solvent to extract CB compounds and other tissue components. Analytical purification of such an extract provides pharmaceutical grade CB compounds. Alternatively, CB compounds are extracted from plant tissue under supercritical conditions. Solvents used for supercritical extraction of CBs include, for instance: carbon dioxide, or other gases in isolation or combination with or without solvent modifiers, selected from ethanol, propanol, butanol, hexane, chloroform, dichloromethane, acetone, or any organic solvent capable of extracting CBs, and alcohol-water mixtures, such as water-ethanol or water-butanol mixtures, etc.

The present invention, in one embodiment, involves producing an extract from Cannabis plant matter, containing THC, CBD and optionally the carboxylic acids thereof. In one embodiment, the dried plant matter is ground and subjected to a CO2 extraction and the primary extract obtained is separated. Specifically, ground Cannabis plant material is compressed and charged into an extraction vessel. CO2 is then introduced, having been brought to a temperature, in one embodiment, of approximately 60° C. and to a pressure of approximately 250 bars. When the CO2 enters into contact with the material to be extracted, it extracts the desired CB components, in particular comprising $\Delta 9$-THC and CBD, as well as the carboxylic acids thereof. In one embodiment, the extraction method permits extracting various isomers of THC, selectively obtained from industrial hemp and from drug-producing hemp, also separating undesirable waxes and removing the solvent.

The CBs, including THC, can be isolated from Cannabis plants using extraction methods or can be made synthetically or semi-synthetically. It is preferable, in one embodiment, that the extraction/production method yields substantially the $(-)-\Delta^9$-trans-THC isomer that is the most active isomer of THC. There are also various techniques that are known for isolating and separating the $(-)-\Delta^9$-trans-THC isomer from other compounds in THC. For example, U.S. Pat. No. 7,449,589 describes methods for purifying the $(-)-\Delta^9$-trans-THC isomer from a mixture of other THC isomers (U.S. Pat. No. 7,449,589, 2004).

However, THC, and in particular the $(-)-\Delta^9$-trans-THC isomer, is not very stable. Also, chemical synthesis and isolation of $(-)-\Delta^9$-trans-THC are both challenging. Further, the $(-)-\Delta^9$-trans-THC isomer is prone to acid-catalysed isomerization to the $\Delta^8$-THC isomer, it is easily oxidized by oxygen to form inactive cannibinol, and it is also sensitive to light and heat. All of these factors make it difficult to synthesize, purify, and store a high purity THC compound comprising the $(-)-\Delta^9$-trans-THC isomer that will be stable over time and under various storage conditions.

It is not the purpose of this disclosure to provide particulars concerning the attainment of a colloidal formulation that is stable under a range of conditions. Though, in one embodiment, the disclosed compound with initial purity (HPLC) of mitragynine, 7-hydroxymitragynine, and delta-9-THC being at least 98% by area can achieve stability such that at least 95% by area remains in undegraded form after exposure of the compound to the storage conditions for twelve months, where the ambient temperature is between 20° C. and 40° C. and relative humidity is between 55% and 75%.

In one embodiment, the stability of said compound is attained by contacting a solution containing mitragynine, 7-hydroxymitragynine, and delta-9-THC into a solvent such as organic solvents, including acetone, acetic acid, alcohols, chloroform, diethyl ether solvents, and other solvents that can be used to dissolve said alkaloids; and in another embodiment, with addition of pharmaceutically acceptable buffers, stabilizers, and other pharmacologically inactive substances.

In one embodiment, the inventive compound is present in the form of micelles or liposomes that encapsulate mitragynine, 7-hydroxymitragynine, THC, CBD, and/or other alkaloids within the membrane of the micelles or liposomes. Within the context of the present technology, the term "micelle" refers to an aggregate of surfactant molecules dispersed in a liquid colloid, while "liposome" refers to a vesicle composed of a mono or bilayer lipid.

In yet another embodiment, other drugs, and pharmaceutically acceptable carriers, if present, may be in the lipophilic membrane or entrapped in the aqueous fluid that forms the core of the liposome. The entrapped alkaloids contribute to the stability of the micelle/liposome membranes, such that the micelle/liposomes formulations may be used as an improved, fast, reliable and efficient system for the oral, enteral, parenteral, intravenous or topical delivery of mitragynine, pseudoindoxyl, 7-hydroxymitragynine, delta-9-THC, and/or other alkaloids, and/or additional drugs to subjects in need thereof.

In another embodiment, unilamellar micelles or liposomes that are thermostable at temperatures greater than 50° C. are used in the manufacture of the compound contemplated by this invention. These micelles or liposomes are obtained by contacting a solution of *Mitragyna speciosa* and *Cannabis sativa* plants alkaloids with an appropriate solvent. The mixing of said alkaloid solution occurs in a manner suitable for the rapid dissolution of the alkaloid solution. This can be accomplished through a variety of means including dilution, injection through a small orifice under pressure, and ultrasonic atomization.

And yet in another embodiment, the disclosed compound has advantageous properties, where the micellar and liposomal compound is stable at high temperatures, exceeding 50° C., is stable to sonication, capable of carrying large payloads of *Mitragyna speciosa* and *Cannabis sativa* plants alkaloids as well as other drugs suitable for use in combination therapy and can be stored for extended periods of time, for example greater than 20 weeks at 25° C.

In certain embodiments, said compound can be in the form of a concentrated, stable colloidal suspension that is obtained by infusing a solvent solution containing the *Mitragyna speciosa* and *Cannabis sativa* plants extract or essentially pure alkaloids into a solvent, with or without buffer. Stabilizing agent, for instance, a polymer or compounds selected from cellulose hyaluronic acid, citric acid, Tris base, sodium carbonate, polyvinyl pyrrolidone (PVP), alginate, chondritin sulfate, poly gamma glutamic acid, gelatin, chitisin, corn starch and flour can be used to stabilize the micelle formulations.

In one embodiment, said compound also exhibits superior systemic delivery and release of *Mitragyna speciosa* and *Cannabis sativa* plants alkaloids from the micelle or liposomes used in the manufacture of the contemplated compound. The release of alkaloids from a liposome or micelle of the contemplated compound can be modulated by changing the ratio of the concentration of lipid to the concentration of alkaloids present in the liposome.

In one embodiment, tissue specific delivery can be achieved by modifying the surface of the liposomes or micelles with compounds that bind specifically to biological macromolecules expressed on cellular surfaces. For instance, the micelle or liposomal surface can be derivatized to display an antibody specific to an antigen expressed on cancer cells.

According to one embodiment, said compound that is used in the treatment of a disease condition or other therapy is administered to a patient or subject in need of treatment either alone or in combination with other compounds/drugs having similar or different biological activities. For example, said compound may be administered in a combination therapy, i.e., either simultaneously in single or separate dosage forms or in separate dosage forms within hours or days of each other. Examples of compounds/drugs used in such combination therapies include without limitation: chemotherapeutic agents, immunosuppressive agents, immunostimulatory, anti-pyretic, cytokines, opioids, cannabinoids, cytokines, cytotoxic agents, nucleolytic compounds, radioactive isotopes, receptors, pro-drug activating enzymes, which may be naturally occurring or produced by recombinant methods, anti-inflammatory agents, antibiotics, protease inhibitors, growth factors, osteo-inductive factors and the like.

In some embodiments, the compound further contains, in accordance with accepted practices of pharmaceutical compounding, one or more pharmaceutically acceptable excipients, including without limitation: diluents, adjuvants, stabilizers, emulsifiers, preservatives, colorants, buffers, flavor imparting agents. As stated above, said compound contains *Mitragyna speciosa* and *Cannabis sativa* plants alkaloids, their analogs (such as: levonantradol; CP 47,497; (C6)-CP 47,497; (C8)-CP 47,497; (C9)-CP 47,497; CP 50,556-1; CP 55,244; CP 55,940; CP-945,598; HHC; O-1871; AMG-36; AMG-41; AM-694; AM-906; AM-1235; AM-2232; AM-2233; AM-2389 O-1812; THJ-2201; JWH-018 and other cannabinoid receptor agonists), and co-extraction substances, and may be consumed directly or formulated into nutraceutical or pharmaceutically acceptable compounds suitable for oral, enteral, parenteral, intravenous or topical administration.

The term "parenteral" as used herein includes subcutaneous injections, intravenous, intramuscular, intrasternal injection or infusion techniques. Such excipients are well-known in the art. Dosage forms for oral administration include food, beverages, drinks, soups, baked goods, syrups, oral pharmaceutical compounds, nutraceutical formulations, and the like. Suitable pharmaceutical carriers include any such materials known in the art, e.g., any liquid, gel, solvent, liquid diluent, solubilizer, polymer or the like, which does not significantly interact with other components of the formulations in a deleterious manner.

Liquid dosage forms for oral administration include, but are not limited to, pharmaceutically acceptable emulsions, solutions, suspensions, syrups and elixirs. In addition to the *Mitragyna speciosa* and *Cannabis sativa* plants extract, the liquid dosage forms can contain inert diluents commonly used in the art. For instance, liquid formulations can contain water, alcohol, polyethylene glycol ethers, and any other pharmaceutically acceptable solvents. Solubilizing agents and emulsifiers such as, without limitation: ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols, fatty acid esters of sorbitan and mixtures thereof may also be present in said compound.

Additionally, oral compound of the proposed invention can include, without limitation, adjuvants such as wetting agents, emulsifying and suspending agents, sweetening, flavoring, and perfuming agents. When formulated as a suspension, said compound may contain the *Mitragyna speciosa* and *Cannabis sativa* plants extract and suspending agents, for example, without limitation: ethoxylated isostearyl alcohols, polyoxyethylene sorbitol, sorbitan esters, microcrystalline cellulose, aluminum metahydroxide, bentonite, agar-agar, tragacanth, and mixtures thereof.

In one embodiment, the emulsifier may comprise a mixture of monoglyceride and diglyceride at a total concentration of 1% to 99% w/w and a carrageenan or mixture of carrageenans at a total concentration of 0.01% to 10% w/w. In another embodiment, the emulsifier may be present in a concentration range of 1% to 99%, 5% to 80%, 10% to 35%, 10% to 20%, or about 15%-25%% w/w.

Solid dosage forms suitable for oral administration include, capsules, tablets, pills, powders, and granules. In such solid dosage forms, the *Mitragyna speciosa* and *Cannabis sativa* plants extract can be used alone or in combination with one or more drugs that are mixed with at least one pharmaceutically acceptable excipient or carrier such as sodium citrate or dicalcium phosphate and/or fillers or extenders such as starches, lactose, sucrose, glucose, mannitol, and silicic acid; binders such as, for example, carboxymethylcellulose, alginates, gelatin, polyvinylpyrrolidone, sucrose, and acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as, for example, acetyl alcohol and glycerol monostearate; absorbents such as kaolin and bentonite clay; and lubricants such as talc, calcium stearate, magnesium stearate, solid polyethylene glycols, sodium lauryl sulfate, and mixtures thereof. For capsules, tablets and pills, the dosage form can also comprise buffering agents, such as acetic acid and Tris base.

Micellular or liposomal suspensions can be encapsulated with a variety of polymers, sugars, and chelating agents, to yield stable solid preparation. Encapsulation can take the form of cross linked polymers, trapping of the micells or liposomes within a non-crosslinked polymer network, or dispersed within the crystalline structure of sugar starches or protein molecules. These granules can be further processed to yield sublingual films, suppositories, dispersible powder, tablets, gel capsules, etc.

Solid dosages in the form of tablets, capsules, pills, and granules can be coated using compounds that accelerate or decrease the release of alkaloids. For instance, the proposed invention also encompasses solid dosage forms having enteric coatings, extended-release coatings, sustained-release coatings, delayed release coatings and immediate-release coatings. Methods used to coat solid dosage forms as well as the materials used to manufacture such coatings are well known in the pharmaceutical formulary art. The solid dosage forms can optionally contain opacity enhancing agents. According to one embodiment, the solid dosage form comprises an enteric coating that permits the release of *Mitragyna speciosa* and Cannabis *sativa* plants alkaloids or their analogs alone or in combination with one or more drugs, or other *Mitragyna speciosa* and/or *Cannabis sativa* plants alkaloids, at a specific location within the gastrointestinal tract, optionally, in a delayed manner. Exemplary of such coating materials include glyceryl monostearate or glyceryl distearate may be employed, polymeric substances and waxes. The compound contemplated by this invention, alone or in combination with one or more drugs, can also be in micro-encapsulated form, if appropriate, with one or more of the above-mentioned or other excipients.

In one embodiment, said compound is packaged into a gelatin capsule dosage form. In another embodiment, the compound is packaged into a non-gelatin capsule or an HPMC capsule. Said capsule can be a vegan based capsule or else. The compound disclosed herein includes a sustained release compound, an immediate release compound, or a combined sustained release fraction and immediate release fraction. In one embodiment, the therapeutic effect of the compound has a duration up to 4 hours, up to 6 hours, up to 8 hours, up to 10 hours, up to 12 hours, up to 14 hours, up to 16 hours, up to 18 hours, or up to 24 hours. In one embodiment, the compound disclosed herein comprises an immediate release fraction and a sustained release fraction, wherein the immediate release fraction contains a therapeutically effective amount of *Mitragyna speciosa* and *Cannabis sativa* plants alkaloids and an edible oil; and wherein the sustained release fraction contains a therapeutically effective amount of *Mitragyna speciosa* and *Cannabis sativa* plants alkaloids, and a mixture of emulsifiers and other pharmacologically inactive substances.

In another embodiment, a dietary compound, according to the present invention, is any ingestible preparation that contains the *Mitragyna speciosa* and *Cannabis sativa* plants extract as contemplated by this invention, where the pharmacologically inactive substance is a food product. The food product can be dried, cooked, boiled, lyophilized, baked, frozen, chilled, liquid, semi-liquid or prepared by any preparation used in food processing. Such food product can be, but not limited to: breads, teas, soups, cereals, salads, sandwiches, sprouts, vegetables, animal feed, pills and tablets, soft drinks, instant drinks, and any other human or animal food.

In yet another embodiment, a compound for parenteral injection comprises pharmaceutically acceptable sterile aqueous or non-aqueous solutions, dispersions, suspensions or emulsions as well as sterile powders for reconstitution into sterile injectable solutions or dispersions prior to use. Examples of suitable aqueous and non-aqueous carriers, diluents, solvents or vehicles include, without limitation, water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate.

In one embodiment, proper fluidity can be maintained, for example, by the use of coating materials such as lecithin, by the maintenance of the required particle size in the case of dispersions, and by the use of surfactants. The compound of the present invention can also contain adjuvants such as, but not limited to, preservatives, wetting agents, emulsifying agents, and dispersing agents. The compound for parenteral delivery generally includes isotonic agents such as sugars, sodium chloride, and the like. Prolonged absorption of the injectable pharmaceutical formulation can be brought about by the inclusion of agents which delay absorption such as aluminum monostearate and gelatin.

Injectable depot forms are made, in one embodiment, by forming microencapsule matrices of the drug in biodegradable polymers such as polylactide-polyglycolide. Depending upon the ratio of drug to polymer and the nature of the specific polymer employed, the rate of drug release can be controlled. Examples of other biodegradable polymers include poly-orthoesters and poly-anhydrides. Depot injectable formulations are also prepared by entrapping the drug in liposomes or microemulsions which are compatible with body tissues. The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Dosage forms for topical administration include, but are not limited to, ointments, creams, emulsions, lotions, gels, sunscreens and agents that favor penetration within the epidermis. Various additives, known to those skilled in the art, may be included in the topical formulations of the invention. Examples of additives include, but are not limited to, solubilizers, skin permeation enhancers, preservatives (e.g., anti-oxidants), moisturizers, gelling agents, buffering agents, surfactants, emulsifiers, emollients, thickening agents, stabilizers, humectants, dispersing agents and pharmaceutical carriers. Examples of moisturizers include jojoba oil and evening primrose oil.

Suitable skin permeation enhancers are well known in the art and include lower alkanols, such as methanol ethanol and 2-propanol; alkyl methyl sulfoxides such as dimethylsulfoxide (DMSO), decylmethylsulfoxide (C10 MSO) and tetradecylmethyl sulfoxide; pyrrolidones, urea; N,N-diethyl-m-toluamide; C2-C6 alkanediols; dimethyl formamide (DMF), N,N-dimethylacetamide (DMA) and tetrahydrofurfuryl alcohol. Examples of solubilizers include, but are not limited to, hydrophilic ethers such as diethylene glycol monoethyl ether (ethoxydiglycol, available commercially as Transcutol) and diethylene glycol monoethyl ether oleate (available commercially as Softcutol); polyoxy 35 castor oil, polyoxy 40 hydrogenated castor oil, polyethylene glycol (PEG), particularly low molecular weight PEGs, such as PEG 300 and PEG 400, and polyethylene glycol derivatives such as PEG-8 caprylic/capric glycerides (available commercially as Labrasol); alkyl methyl sulfoxides, such as DMSO; pyrrolidones, DMA, and mixtures thereof.

Prevention and/or treatment of infections can be achieved by the inclusion of antibiotics, as well as various antibacterial and antifungal agents, for example, paraben, chlorobutanol, phenol sorbic acid, and the like, in the compounds of the invention.

One of ordinary skill will appreciate that effective amounts of the agents in the compound used in the methods of the invention can be determined empirically. It will be understood that, when administered to a patient, the total daily usage of the compound of the present invention will be decided by the attending physician within the scope of sound medical judgment. The specific therapeutically effective dose level for any patient will depend upon a variety of factors: the type and degree of the response to be achieved; the activity of the specific compound employed; the age, body weight, general health, sex and diet of the patient; the duration of the treatment; drugs used in combination or coincidental with the method of the invention; and like factors well known in the medical arts.

Tetrahydrocannabinol (THC) is one of many cannabinoids identified in Cannabis *sativa* and it is the main psychoactive alkaloid. At smaller doses, THC produces euphoria, relief of anxiety, sedation and drowsiness. In some respects, the effects are similar to those caused by alcohol. Lemberger et al., (1973) found that in man, $\Delta^9$-THC is converted to 11-OH-$\Delta^9$--THC, which is in part responsible for the psychologic effects.

THC (C21H3002), also known as $\Delta$9-THC and $\Delta$9-tetrahydrocannabinol, is the major active principle in all cannabis products. Its International Non-Proprietary Name (INN) is dronabinol. The unsaturated bond in the cyclohexene ring is located between C-9 and C-10 in the more common dibenzopyran ring numbering system. There are four stereoisomers of THC, but only the (–)-trans isomer occurs naturally (CAS-1972-08-03). The fully systematic name for this THC isomer is (–)-(6aR,10aR)-6,6,9-trimethyl-3-pentyl-6a,7,8,10a-tetrahydro-6H-benzo[c]chromen-1-ol. Two related substances, $\Delta$9-tetrahydrocannabinol-2-oic acid and $\Delta$9-tetrahydrocannabinol-4-oic acid (THCA), are also present in cannabis, sometimes in large amounts. The active isomer $\Delta$8-THC, in which the unsaturated bond in the cyclohexene ring is located between C-8 and C-9, is found in much smaller amounts. The boiling point of THC is 314.6° F. (157° C.), metabolism is mostly hepatic by CYP2C, biological half-life is 1.6-59 h, 25-36 h (orally administered dronabinol), bioavailability: 10-35% (inhalation), 6-20% (oral), and excretion is 65-80% (feces), 20-35% (urine) as acid metabolites.

Cannabinoids were found to be effective analgesics in animal models with non-opiate mechanisms predominating. There are many anecdotal reports (Grinspoon & Bakalar, 1993) of benefits in bone and joint pain, migraine, cancer pain, menstrual cramps and labor. Many recreational smokers receiving cancer chemotherapy have told their doctors that cannabis relieved their nausea. Sallan et al., (1975) in a randomized control trial (RCT) compared oral THC and placebo in 22 cancer patients who had proved resistant to conventional anti-emetics. Comparisons using patients' self-reports of nausea and vomiting demonstrated that THC was statistically superior to placebo. THC (10 mg/m2) produced euphoria in the majority of patients, and one-third experienced sedation.

Metanalysis of THC had revealed poor or partial response to THC in approximately 65% of 750 courses of oral therapy conducted by Plasse et al. (1991). This could be due to administering a high single dose of THC, which may cause undesirable side effects, such as sedation, confusion and anxiety. Poor response to oral administration of THC may be due to the limited aqueous solubility of THC, its extensive first pass metabolism following oral administration, and the resulting low absolute bioavailability (13% on an average). Pharmacokinetic studies had indicated that THC bioavailability is only 10-20% in healthy adults, and this may be further decreased by emetic episodes in patients. In addition, it has been noted that fasting or food deprivation could decrease the rate of absorption of THC from sesame oil capsules currently available in the market. Previous studies have also reported that another limitation of orally administered THC is the large intrasubject variability in absorption. For this reason, it would be important to titrate the THC dose on an individual basis, since the drug has biphasic activity and a relatively narrow therapeutic index.

The median lethal dose (LD50) of oral THC in rats was 800 to 1900 mg/kg depending on sex and strain (Thompson, Rosenkrantz, Schaeppi, & Braude, 1973). Specifically, LD50 was 1270 mg/kg for males and 730 mg/kg for females administered orally (dissolved in sesame oil). If this was scaled up to an adult human, the LD50 would be 50-86 g for 150 lb., female or male, respectively, or ~1 kg of 10% THC content taken orally. Such low LD50 is explained by low number of CB1 receptors located in the brain parts that control vital functions such as respiration. There were no cases of death due to toxicity following the maximum THC dose in dogs (up to 3000 mg/kg THC) and monkeys (up to 9000 mg/kg THC). Chan et al., (1996) administered 50 mg/kg THC to rats for a period of two (2) years.

The long-term use toxicity of THC and CBD mixture (27 mg/mL and 25 mg/mL) in human patients is shown in FIG. 6. According to the study conducted by Wade et al., (2006) it represents the median intoxication scores (displaying the 10th and 90th percentiles which represents the central 80% of data) for 92 patients completing at least 48 weeks of treatment. According to Fitzgerald et al., (2013) the minimum lethal oral dose for dogs for THC is more than 3 g/kg. Animal studies have shown a very large separation (by a factor of more than 10,000) between pharmacologically effective and lethal doses. A comparative risk assessment of drugs including alcohol and tobacco using the margin of exposure (MOE) approach was conducted. The toxicological MOE approach validated epidemiological and social science-based drug ranking approaches especially in regard to the positions of alcohol and tobacco (high risk) and cannabis (low risk).

The effects of cannabis are dose dependent. The most frequently reported adverse effects are mental slowness, impaired reaction times, and sometimes accentuation of anxiety. Serious psychological disorders have been reported with high levels of intoxication (Kalant, 2004). A causal role of acute cannabis intoxication in motor vehicle and other accidents has now been shown by the presence of measurable levels of THC in the blood of injured drivers in the absence of alcohol or other drugs. Several different studies indicate that the epidemiological link between cannabis use and schizophrenia probably represents a causal role of cannabis in precipitating the onset or relapse of schizophrenia. According to Kalant (2004), a weaker but significant link between cannabis and depression has been found in various cohort studies, but the nature of the link is not yet clear.

According to Kalant (2004), a large body of evidence now demonstrates that cannabis dependence, both behavioral and physical, does occur in about 7-10% of regular users, and that early onset of use, and especially of weekly or daily use, is a strong predictor of future dependence. Cognitive impairments of various types are readily demonstrable during acute cannabis intoxication, but there is no suitable evidence yet available to permit a decision as to whether long-lasting or permanent functional losses can result from chronic heavy use in adults (Kalant, 2004). However, according to Kalant (2004), a small but growing body of evidence indicates subtle but apparently permanent effects on memory, information processing, and executive functions, in the offspring of women who used cannabis during pregnancy. Kalant (2004) concludes that evidence indicates that regular heavy use of cannabis carries significant risks for the individual user and for the health care system.

The pharmacological effects of Kratom are mainly attributed to its principal alkaloid mitragynine and 7-hydroxymitragynine (FIG. 5). Mitragynine is the most abundant alkaloid in the leaves. It was first isolated in 1921 and its chemical structure was fully elucidated in 1964. The systematic (Chemical Abstract) name is (aE,2S,3S,12bS)-3-ethyl-1,2,3,4,6,7,12,12b-octahydro-8-methoxy-α-(methoxymethylene)-indolo[2,3-a]quinolizine-2-acetic acid methyl ester (CAS Registry Number: 4098-40-2). Other names: (E)-16,17-didehydro-9,17-dimethoxy-17,18-seco-20α-yohimban-16-carboxylic acid methyl ester, 9-methoxy-corynantheidine, and SK&F 12711. Mitragynine is poorly soluble in water but soluble in conventional organic solvents, including acetone, acetic acid, alcohols, chloroform and diethyl ether providing fluorescent solutions. Mitragynine distils at 230-240° C. at 5 mmHg. It forms white, amorphous crystals that melt at 102-106° C. The melting point of mitragynine hydrochloric acid salt is 243° C.; the picrate melts at 223-224° C. and the acetate at 142° C.

The 7-Hydroxymitragynine (FIG. 5) is present in small amounts in Kratom leaves and was identified in 1993. Its systematic (Chemical Abstract) name is (αE,2S,3S,7aS,12bS)-3-ethyl-1,2,3,4,6,7,7a,12b-octahydro-7a-hydroxy-8-methoxy-α-(methoxymethyl ene)-indolo[2,3-a]quinolizine-2-acetic acid methyl ester (CAS Registry Number: 174418-82-7). On average, *Mitragyna speciosa* plant extract contains less than 2% of said substance.

The chemical total syntheses reported for several Kratom alkaloids are too complex to be used for economic production of these compounds. However, mitragynine can serve as a chemical precursor to the more potent 7-hydroxymitragynine. The synthesis of mitragynine can be achieved using one of the available techniques; for example, the total synthesis proposed by Ma, et al., (2007) using an enantiospecific method for the synthesis of mitragynine, as well as 4-methoxytryptophan, 9-methoxygeissoschizol, and 9-methoxy-Nb-methylgeissoschizol via a regiospecific Larock heteroannulation, the asymmetric Pictet-Spengler reaction, and a Ni(COD)2 mediated cyclization serving as key steps.

According to Ramanathan, et al. (2015), several pharmacological studies have been undertaken on rodents. However, the mitragynine dose employed in these studies varied largely across rodent species: analgesic (30-200 mg/kg), pharmacokinetics (20-50 mg/kg), toxicity (200-477 mg/kg). Others reported no toxicity even at mitragynine dose levels of 800-900 mg/kg in rodents. However, a study by Janchawee et al. (2007) demonstrated lethal effects after an oral administration of 200 mg/kg mitragynine in rats. The similar fatal effect was also observed after administration of 200 mg/kg alkaloid extract of Kratom to rats (Azizi, Ismail, Mordi, & Ramanathan, 2010).

According to Ramanathan, et al. (2015), as mentioned above, varied pharmacological responses have been reported for mitragynine in the literature, but no supportive scientific explanations have been given for this. Ramanathan, et al. (2015), have undertaken a study to understand the physicochemical properties of mitragynine. In their work, a UV spectrophotometer approach and HPLC-UV methods were employed to ascertain the physicochemical properties of mitragynine. The pKa of mitragynine measured by conventional UV (8.11±0.11) was in agreement with the microplate reader determination (8.08±0.04). Ramanathan, et al. (2015), concluded that mitragynine is a lipophilic alkaloid, as indicated by a log P value of 1.73.

Similar to THC, mitragynine has poor solubility in water and basic media, and conversely in acidic environments, but it is acid labile (Ramanathan, et al., 2015). In an in vitro dissolution the total drug release was higher for the simulated gastric fluid (SGF) but was prolonged and incomplete for the simulated intestinal fluid (SIF). FIG. 3 shows dissolution profiles of mitragynine in SIF and SGF. The hydrophobicity, poor water solubility, high variability of substance release in simulated biological fluids and acid-degradable characteristics of mitragynine probably explain the large variability of its pharmacological responses reported in the literature (Ramanathan, et al., 2015). This invention intends to overcome these problems and provides a basis for developing a suitable formulation to improve its solubility, stability and oral absorption.

It is likely that mitragynine is better absorbed in the basic environment of the intestine owing to its lipophilic nature and the fact it predominantly exists in non-ionized form. However, it is an acid labile drug and requires protection from acidic gastric juice when the drug is administered orally. In recognition of these physicochemical properties and to further improve its solubility, stability and to achieve uniformity in oral absorption, incorporation of mitragynine into a lipid carrier is essential. Though it is poorly water soluble (<100 µg/mL), the drug showed some reasonable degree of solubility in lipid (log P: 1.70). In one embodiment, employing techniques such as solid dispersion and by incorporating mitragynine into lipid carriers, its solubility in aqueous media could be improved, since this vehicle acts by self-emulsifying the drug particles into fine divided state and simultaneously protects it from acid degrading (Ramanathan, et al., 2015).

Trakulsrichai et al. (2015), conducted a study of mitragynine pharmacokinetics in man. Ten chronic, regular, healthy users of Kratom were enrolled and the dose was adjusted to a steady state in each subject by giving a known amount of Kratom tea for 7 days before commencement of the experiment. During the study, Trakulsrichai et al. (2015), have admitted and gave different oral doses to subjects to confirm linearity in pharmacokinetics. The mitragynine blood concentration was measured at 17-time points and the urine concentration was measured during 24-hour period by liquid chromatography-tandem mass spectrometry method.

According to Trakulsrichai et al. (2015), ten male subjects completed the study without adverse effects. From data of nine subjects (one analyzed separately due to the abnormal blood concentration data), the pharmacokinetic parameters established were as follows: time to reach the maximum plasma concentration is 0.83±0.35-hour, terminal half-life is 23.24±16.07 hours, and the apparent volume of distribution is 38.04±24.32 L/kg. FIG. 4 illustrates plasma mitragynine concentration-time curve of the subjects after the administration of a loading dose: the normal plot (upper chart) and semi-logarithmic plot (lower chart). The urine excretion of unchanged form was 0.14%. The pharmacokinetics were observed to be oral two-compartment model. Trakulsrichai et al. (2015), concluded that, "Even if Kratom is mainly available as a drug of abuse, it may yet provide insight into the possibility for its medicinal development as a new and more effective opioid substitute or pain killer in the future, with fewer lethal side effects."

Another study (Trakulsrichai, et al., 2013) was designed to identify the characteristics of Kratom poisoning and withdrawal cases from Kratom exposure cases in Ramathibodi Poison Center (RPC), Thailand, during a five-year period. The study provides a retrospective review of Kratom exposure cases from the RPC toxic surveillance system. A total of 52 Kratom exposure cases were identified. There were Kratom poisoning cases (76.9%) and withdrawal cases (23.1%). Common presenting symptoms in the poisoning group were palpitation (22.5%), followed by seizure (17.5%). For the withdrawal group, the common presenting symptoms were myalgia (33.3%), insomnia (16.67%), fatigue (16.67%), and chest discomfort (16.67%). Trakulsrichai, et al., (2013) notes that there was a case of baby with withdrawal symptoms who was delivered from a chronic Kratom-abusing mother, suggesting possible exposure via the transplacental route. There were no deaths in either group. Kratom abuse can cause either poisoning or withdrawal. Most cases in both groups had good prognostic outcome (Trakulsrichai, et al., 2013).

It was also reported in a different study that a man who tried to abstain from Kratom had difficulty sleeping, wriggling sensation in the shoulders and the back, dragging sensation in the hips, bitemporal headache, became extremely weak and also had difficulty walking (Thuan, 1957). A study by Vicknasingam and colleagues (2010) also revealed that kratom produced mild side effects such as loss of weight, dehydration, constipation but no other medical problems were reported. However, prolonged use of kratom was reported to cause adverse effects which include nausea, diarrhea, vomiting, hallucinations, psychosis, agitation, dizziness, itching, sweating, dry mouth, respiratory depression, constipation, anorexia, increased urination, palpitations and weight loss (Suwanlert, 1975) (Jansen & Prast, 1988) (Babu, McCurdy, & Boyer, 2008) (Adkins, Boyer, & McCurdy, 2011). Other than adverse effects, there are no reports of mortalities following mitragynine or Kratom consumption alone, even after chronic and high dosage consumption (Ramanathan & Mansor, 2014).

In a series of 9 lethal cases from Sweden, both mitragynine (0.02-0.18 g/g) and O-desmethyltramadol (0.4-4.3 g/g) were detected in the post mortem blood samples of Krypton (powdered Kratom mixed with the u-opioid receptor agonist, O-desmethyltramadol, an active metabolite of Tramadol) users over a 1-year time. It was suggested that the addition of both, u-opioid receptor agonists, mitragynine and O-desmethyltramadol, to the herbal mixture may have caused the unintentional death. However, since no data for lethal doses in humans are available yet, the contribution of mitragynine to polytoxic causes of death is currently hard to estimate (Holler, et al., 2011).

Although Kratom seems to be safe when administered at 1-10 mg/kg doses (which represents a sub-chronic dose), according to Pantano (2016), after prolonged exposure to a 100 mg/kg dose, as demonstrated in the experiments on Sprague-Dawley rats conducted by Sabetghadam et al. (2013), it causes biochemical and hematological changes with histopathological alterations in several tissues (liver, kidney and brain). Another study reported that Kratom users consume about 67.5-75 mg of Kratom per day and that no adverse effects were shown while only after prolonged exposure to a higher dose of Kratom, clinical signs of toxicity were highlighted (Vicknasingam B., Narayanan, Beng, & Mansor, 2010). Only a few papers (Kapp, Maurer, Auwarter, Winkelmann, & Hermanns-Clausen, 2011), according to Pantano (2016), report liver damages or hepatotoxic sequelae related to Kratom use, and also in these cases, the authors highlighted the difficulties of a correlation between Kratom consumption and hepatic injuries, which was more likely to be associated with the extraction process of the alkaloids or to the presence of contaminants in the herbal products (Raffa, 2014). Moreover, causality has not yet been accurately established for Kratom, as CIOMS scale (RUCAM) has not been applied to suspected cases (Pantano, et al., 2016).

The formulations of the invention, in one embodiment, are particularly suitable for oral administration and may be administered to subjects with a new or pre-existing condition or pre-disposed to certain disease conditions, or under certain circumstances, such as without limitation: HD; Wilson's Disease; PD; metabolic and endocrine diseases and disorders; athetosis-related to damage or degeneration of basal ganglia; minor tranquilizers, alcohol, cocaine, (meta) amphetamine, and opioid withdrawal syndromes; symptoms or side effects associated with anti-retroviral therapy, chemotherapy and radiation therapy; AIDS; rheumatoid arthritis; osteoarthritis; fibromyalgia; pain and spasticity symptoms associated with MS, Neuromuscular Junction Disorder, or other neurodegenerative dieses, autoimmune diseases and disorders, motor neuron diseases and disorders, neurodegenerative diseases and disorders; pain associated with cancer; trauma; athletic performance enhancement; migraine; surgical intervention or medical treatment; stroke; heart attack; dental and gum-related pain; abdominal pain; bone pain, muscle pain; neurological pain; stomach ulcers-related pain; gallbladder disease-related pain; Central Pain Syndrome; sports trauma; obesity-associated treatment; chronic pain disorder (nociceptive pain, neuropathic pain, chronic back or leg pain, painful neuropathies, Complex Regional Pain Syndrome), and acute pain.

In addition to analgesic effects, methanolic *Mitragyna speciosa* plant extract may demonstrate anti-inflammatory effects. Inflammation is a response to pathogens, chemical or mechanical injury, or based on neurogenic loops (neurogenic inflammation). According to Shaik Mossadeq et al. (2009), an intraperitoneal administration of an *Mitragyna speciosa* plant extract was able to inhibit the development of a carrageenan induced paw oedema with a maximal inhibition during first 3 hours after the challenge. The extract may exert its anti-inflammatory effect by inhibiting the synthesis, release and action of a number of hyperalgesic mediators. Thereby, it suppresses the early phase of the oedema, which is the characteristic of acute inflammation. Arachidonic acid and its metabolites according to Shaik Mossadeq et al. (2009), might be responsible for the inhibitory activity of the extract for a period of 4 hours. Daily administration of the *Mitragyna speciosa* plant extract, according to Shaik Mossadeq et al. (2009), was also able to inhibit the growth of granuloma tissue as characterized by proliferation of modified macrophages, fibroblasts and highly vascularized and reddened mass tissue. The authors suggested that inhibition of pro-inflammatory mediator release and vascular permeability in combination with enhanced immunity, stimulation of tissue repair and healing processes may have contributed to the anti-inflammatory properties of *Mitragyna speciosa* (Shaik Mossadeq, et al., 2009).

Further, according to Kumarnsit et al. (2006), acute and chronically treated rats with *Mitragyna speciosa* plant extract showed a suppression of food and water intake. Also, weight gain was reduced. In a cellular model in rat L8 myotubes, however, according to Purintrapiban et al. (2011), it was shown that *Mitragyna speciosa* preparations increase the rate of glucose uptake and protein levels of glucose transporters, which may contribute to anti-diabetic effects. Central administration of mitragynine into the lateral ventricle did not alter the basal gastric acid secretion, but administration into fourth ventricle of anesthetized rats caused an inhibition of 2-deoxy-D-glucose-stimulated gastric acid secretion in a dose dependent manner. This inhibition was reversed by naloxone indicating the involvement of opioid receptors. The effects of mitragynine, particularly anorexia and weight loss, might be related to direct inhibition of neurons in the lateral hypothalamus (Tsuchiya, et al., 2002). Subcutaneous 7-hydroxymitragynine also caused an inhibition of the gastrointestinal transit in mice (Matsumoto, et al., 2006).

Kratom is known to produce other effects, some of them, as this invention proposes, may be therapeutic. According to Harizal et al. (2010), acute oral administration of 100, 500 and 1000 mg/kg doses of standardized *Mitragyna speciosa* methanolic extract increased blood pressure in rats 1 hour after administration. Chittrakarn et al. (2010), as already mentioned, reported that a methanolic Kratom extract caused muscle relaxation in rats. Thereby, the extract had a greater effect at the neuromuscular junction than on the skeletal muscle or at the somatic nerve. According to Chittrakarn et al. (2010), the Kratom extract and mitragynine (2 mg/mL) blocked the nerve conduction, amplitude and duration of compound nerve action potential. In addition to the above reviewed effects of *Mitragyna speciosa* plant preparation may also interact with the effects of other drugs by changing their metabolism (Hassana, et al., 2013).

According to Hanapi et al. (2010), phase I metabolism involves redox and hydrolysis reactions which are catalyzed by cytochrome P450 enzymes. Hanapi and colleagues (2010) tested the effects of a methanolic *Mitragyna speciosa* extract on the activity of three main CYP450 enzymes, CYP2C9, CYP2D6, and CYP3A4. According to the test, a *Mitragyna speciosa* preparation inhibited the activity of all three tested CYP450s with the most potent effect on CYP2D6.

Overall, *Mitragyna speciosa* extracts and mitragynine have a variety of physiological effects. Present evidence strongly supports analgesic, anti-inflammatory, as well as anorectic effects. Mitragynine and 7-hydroxymitragynine interact with μ-opioid receptors in the CNS. However, a number of these physiological effects appear to be opioid receptor independent and may involve neuronal Ca2+channels and descending noradrenergic and serotonergic projections (Hassana, et al., 2013).

Figure 1:
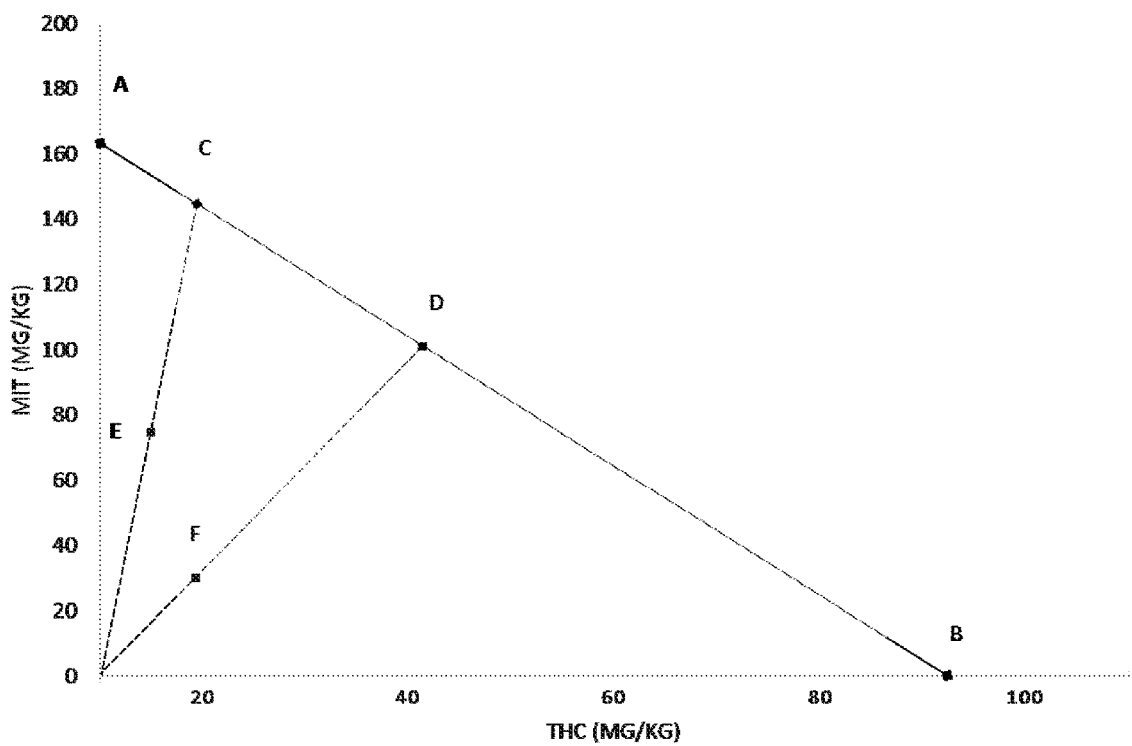

Since multiple pain mechanisms often coexist, especially in the neurological diseases, combining drugs with different but synergistic mechanisms of action, such as cannabinoids and opioids, may produce benefits beyond the individual drugs. Multimodal analgesic practice is well established in acute pain management but less popular with other pain types. It is known that both opioids and cannabinoids have therapeutic and adverse effects that are difficult to separate. However, the inventor proposes, in one embodiment, novel THC/7-hydroxymitragynine, THC/mitragynine, THC/mitragynine pseudoindoxyl combinations, that in another embodiment also include CBD, that may partially overcome these limitations as shown in the FIG. 1. Namely, increased analgesic efficacy of the combination that is also superior to the combination of THC with common opiates such as morphine, and increased safety due to the lower doses necessary for treatment and better safety profile of the aforementioned substances. Evidence exists that increase in safety and medicinal efficacy may be achieved by combining the extracts or specific alkaloids of *Mitragyna speciosa* and *Cannabis sativa*. The potentiation of the analgesic and/or antidepressant effects of mitragynine, 7-hydroxymitragynine and mitragynine pseudoindoxyl is proposed to be via the interaction of cannabinoid system with the opioid system and/or monoamine system, where in one embodiment, mitragynine exhibits an antidepressant effect a contributing factor in controlling certain types of pain.

According to Robson (2001), a number of human small RCTs show that THC is significantly superior to placebo and produces dose-related analgesia peaking at around 5 hours, comparable to but out-lasting that of codeine. Side-effects, according to Robson (2001), were also dose-related, and consisted of slurred speech, sedation and mental clouding, blurred vision, dizziness and ataxia. Levonantradol, a THC analog, was also superior to placebo and notably long-acting, but almost half the patients reported sedation. According to the Institute of Medicine (1999), cannabinoids may have considerable potential in treating neuropathic pain.

Noyes et al., (1975) have conducted a double-blind placebo-controlled study on 10 cancer pain patients, administering 5, 10, 15, and 20 mg of THC. They observed pain relief significantly superior to placebo at doses of 15 and 20 mg. In another double-blind placebo-controlled study, Noyes et al., (1975) have administered to 36 cancer pain patients 20 mg of THC and 120 mg of codeine. They observed that codeine and THC were equally effective, but higher dose of THC sedated most patients, and some found its psychoactive effects uncomfortable. In another double-blind placebo-controlled study, Jain et al., (1981) have administered to 56 patients with postoperative pain 1.5, 2, 2.5, 3 mg intermuscular levonantradol. They observed that all doses were significantly superior to placebo (at least $P<0.05$), but there was no dose-response. 57% of patients reported at least one side-effect, but general acceptability was good, according to Jain et al. (1981). In another double-blind placebo-controlled study, Maurer et al., (1990) have administered to a patient with spinal cord injury 5 mg of THC and 50 mg of codeine. They observed that $\Delta$9-THC and codeine both had an analgesic effect in comparison with placebo. Only THC, however, showed significant effect on spasticity (Maurer, Henn, & Dittrich, 1990). In another double-blind placebo-controlled study, Holdcroft et al., (1997) have administered to a patient with gastro-intestinal (GI) tract pain (familial Mediterranean fever) 50 mg of THC daily. They observed that morphine requirement was significantly reduced ($P<0.01$) during the active treatment (Holdcroft, Smith, & Jacklin, 1997).

In one embodiment of the proposed invention, the treatment of muscle spasms and pain related to an autoimmune disease involves giving to a patient every 12 hours on an empty stomach by oral administration one soft-gel capsule of the compound containing a mixture of 200 mg of mitragynine, and 15 mg of THC; and in another embodiment including 5 mg of 7-hydroxymitragynine; and in another embodiment 30 mg of CBD; and in another embodiment as shown in FIG. 7; and in another embodiment with additional 30 mg of CBG; and in another embodiment, additional 25 mg of paynantheine; and in another embodiment additional 20 mg of speciogynine; and in another embodiment including acetic or ascorbic acid and a number of pharmacologically inactive substances, such as a lipid carrier. Said capsule is an extended release and time-release capsule designed to release said mixture in the small intestine; and in another embodiment, in the stomach. The aforesaid compound and method in some subjects may reduce neurological pain and muscle spasms associated with, in one embodiment, MS, having minimal to nonexistent psychotropic effect. In another embodiment, said compound is administered in conjunction with a therapeutic dose of ajmalicine or another substance, where the medication is taken at bed time.

The potential commercial uses of the disclosed preparations include, for example, protective/prophylactic and medical uses. The compounds of the invention can also be administered by a variety of other routes, including mucosal, subcutaneous and intramuscular administration, and may comprise a variety of carriers or excipients known in the formulary art, such as, non-toxic solid, semisolid or liquid filler, diluent, encapsulating material and formulation auxiliaries that are pharmaceutically acceptable.

The features disclosed in the foregoing description, or the following claims, or the accompanying drawings, expressed in their specific forms or in terms of a means for performing the disclosed function, or a method or system for attaining the disclosed result, as appropriate, may separately, or in any combination of such features, be utilized for realizing the invention in diverse forms thereof.

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments but should be defined in accordance with the following claims and their equivalents.

REFERENCES

Adkins, J. E., Boyer, E. W., & McCurdy, C. R. (2011). *Mitragyna speciosa*, a psychoactive tree from Southeast Asia with opioid activity. *Current Topics in Medicinal Chemistry*, 11, 1165-1175.

Azizi, J., Ismail, S., Mordi, M. N., & Ramanathan, S. (2010). In vitro and in vivo effects of three different *Mitragyna speciosa* Korth leaf extracts on phase II drug metabolizing enzymes—glutathione transferases (GSTs). *Molecules*, 15, 432-441.

Babu, K. M., McCurdy, C. R., & Boyer, E. W. (2008). Opioid receptors and legal highs: *Salvia* divinorum and Kratom. *Clinical Toxicology*, 46(2), 146-152.

Chan, P. C., Sills, R. C., Braun, A. G., Haseman, J. K., & Bucher, J. R. (1996). Toxicity and carcinogenicity of delta 9-tetrahyrocanncinol in Fischer rats and B6C3F1 mice. *Fundamentals and Applied Toxicology*, 109-117.

Chittrakarn, S., Keawpradub, N., Sawangjaroen, K., Kansenalak, S., & Benjamas, J. (2010). The neuromuscular blockade produced by pure alkaloid, mitragynine and methanol extract of kratom leaves (*Mitragyna speciosa* Korth.). *Journal of Ethnopharmacology*, 129, 344-349. Retrieved from http://entheology.com/wp-content/uploads/kratom-research/2010 std008.pdf Fitzgerald, K. T., Bronstein, A. C., & Newquist, K. L. (2013). Marijuana poisoning. *Top Companion Anim Med.*, 8-12. doi:10.1053/j.tcam.2013.03.004.

Formukong, E. A., Evans, A. T., & Evans, F. J. (1988, August). Analgesic and antiinflammatory activity of constituents of *Cannabis sativa* L. *PubMed*, 12(4), 361-371. Retrieved from https://www.ncbi.nlm.nih.gov/pubmed/3169967

Geiser, F., Keenan, J., Rossi, R., Sanchez, A., & Whelan, J. (2004). U.S. Pat. No. 7,449,589.

Grinspoon, L., & Bakalar, J. B. (1993). *Marihuana: The Forbidden Medicine*. New Haven: Yale University Press.

Guy, G., & Robson, P. (2005). U.S. Pat. No. 7,968,594.

Hanapi, N. A., Azizi, J., Ismail, S., & Mansor, S. M. (2010). Evaluation of selected malaysian medicinal plants on phase I drug metabolizing enzymes, CYP2C9 CYP2D6 and CYP3A4 activities in vitro. *International Journal of Pharmacology*, 6, 494-499.

Harizal, S. N., Mansor, S. M., Hasnan, J., Tharakan, J. K., & Abdullah, J. (2010). Acute toxicity study of the standardized methanolic extract of *Mitragyna speciosa* Korth in rodent. *Journal of Ethnopharmacology*, 2, 404-409.

Hassana, Z., Muzaimi, M., Navaratnama, V., Yusoff, N. H., Suhaimi, F. W., Vadivelua, R., . . . Müller, C. P. (2013). From Kratom to mitragynine and its derivatives: Physiological and behavioural effects related to use, abuse, and addiction. *Neuroscience and Biobehavioral Reviews*, 37, 138-151.

Holaday, J. W., & Magistro, P. (2011). U.S. Pat. No. 20,110, 245,287.

Holaday, J. W., & Magistro, P. (2011). U.S. Pat. No. 13,024, 298.

Holdcroft, A., Smith, M., & Jacklin, A. (1997). Pain relief with oral cannabinoids in familial Mediterranean fever. *Anaesthesia*, 12, 44-49.

Holler, J. M., Vorce, S. P., McDonough-Bender, P. C., Magluilo Jr, J., Solomon, C. J., & Levine, B. (2011). A drug toxicity death involving propylhexedrine and mitragynine. *Journal of Analytical Toxicology*, 35, 54-59.

Institute of Medicine. (1999). Cannabinoids and animal physiology. In I. o. Medicine, *Marijuana and Medicine: Assessing the Science Base* (pp. 2.1-2.47). Washington, DC: National Academy Press.

Jain, A. K., Ryan, J. R., & McMahon, F. G. (1981). Evaluation of intramuscular levonantradol and placebo in acute postoperative pain. *Journal of Clinical Pharmacology*, 21((suppl. 8-9)), 320S-326S.

Janchawee, B., Keawpradub, N., Cittrakarn, S., Prasettho, S., Wararatananurak, P., & Sawangjareon, K. (2007). A high-performance liquid chromatographic method for determination of mitragynine in serum and its application to a pharmacokinetic study in rats. *Biomed. Chromatogr.*, 21, 176-183.

Jansen, K. L., & Prast, C. (1988). Ethnopharmacology of kratom and the Mitragyna alkaloids. *Journal of Ethnopharmacology*, 23, 115-119.

Kalant, H. (2004). Adverse effects of cannabis on health: an update of the literature since 1996. *Prog Neuropsychopharmacol Biol Psychiatry*, 28(5), 849-863. doi:10.1016/j.pnpbp.2004.05.027

Kapp, F. G., Maurer, H. H., Auwarter, V., Winkelmann, M., & Hermanns-Clausen, M. (2011). Intrahepatic cholestasis following abuse of powdered kratom (*Mitragyna speciosa*). *J. Med. Toxicol.*, 7, 227-231. doi:10.1007/s13181-011-0155-5

Kruegel, A. C., Gassaway, M. M., Kapoor, A., Varadi, A., Majumdar, S., Filizola, M., . . . Sames, D. (2016). Synthetic and Receptor Signaling Explorations of the Mitragyna. *J Am Chem Soc.*, 138(21), 6754-64. doi: 10.1021/jacs.6b00360

Kumarnsit, E., Keawpradub, N., & Nuankaew, W. (2006). Acute and long-term effects of alkaloid extract of *Mitragyna speciosa* on food and water intake and body weight in rats. *Fitoterapia*, 77, 339-345.

Lemberger, L., Martz, R., Rodda, B., Forney, R., & Rowe, H. (1973). Comparative Pharmacology of Δ9-Tetrahydrocannabinol and its Metabolite, 11-OH-Δ9-Tetrahydrocannabinol. *The Journal of Clinical Investigation*, 52(10), 2411-2417. doi:10.1172/JCI107431

Ma, J., Yin, W., Zhou, H., & Cook, J. M. (2007). *Total Synthesis of the Opioid Agonistic Indole Alkaloid, Mitragynine, as well as the First Total Synthesis of 9-Methoxygeissoschizol and 9-Methoxy-Nb-methylgeissoschizol*. Bethesda: U.S. National Library of Medicine. doi:10.1021/o10712201

Macko, E., Weisbach, J. A., & Douglas, B. (1972). Some observations on the pharmacology of mitragynine. *Arch. Int. Pharmacodyn. Ther.*, 198, 145-161.

Matsumoto, K., Hatori, Y., Murayama, T., Tashima, K., Wongseripipatana, S., Misawa, K., . . . Horie, S. (2006). Involvement of u-opioid receptors in antinociception and inhibition of gastrointestinaltransitinduced by 7-hydroxymitragynine, isolated from Thai herbal medicine *Mitragyna speciosa*. *Journal of Pharmacology*, 549, 63-70.

Matsumoto, K., Horie, S., Ishikawa, H., Takayama, H., Aimi, N., Ponglux, D., & Watanabe, K. (2004). Antinociceptive effect of 7-hydroxymitragynine in mice: Discovery of an orally active opioid analgesic from the Thai medicinal herb *Mitragyna speciosa*. *Life Sci.*, 74(17), 2143-55.

Maurer, M., Henn, V., & Dittrich, A. (1990). Delta-9-tetrahydrocannabinol shows antispastic and analgesic effects in a single case double-blind trial. *European Archives of Psychiatry and Clinical Neuroscience*, 240, 1-4.

Noyes, R. J., Brunk, S. F., & Avery, D. A. (1975). The analgesic properties of delta-9-tetrahydrocannabinol and codeine. *Clinical Pharmacology and Therapeutics*, 18, 84-89.

Noyes, R. J., Brunk, S., & Baram, D. A. (1975). Analgesic effect of delta-9-tetrahydrocannabinol. *Journal of Clinical Pharmacology*, 15, 139-143.

Pantano, F., Tittarelli, R., Mannocchi, G., Zaami, S., Ricci, S., Giorgetti, R., . . . Marinelli, E. (2016). Hepatotoxicity Induced by "the 3Ks": Kava, Kratom and Khat. *Int J Mot Sci.*, 17(4), 580. doi:10.3390/ijms17040580

Plasse, T. F., Gorter, R. W., Krasnow, S. H., Lane, M., Shepard, K. V., & Wadleigh, R. G. (1991). Recent clinical experience with dronabinol. *Pharmacology Biochemistry and Behavior*, 40(3), 695-700. doi:10.1016/0091-3057(91)90385-F Purintrapiban, J., Keawpradub, N., Kansenalak, S., Chittrakarn, S., Janchawee, B., & Sawangjaroen, K. (2011). Study on glucose transport in muscle cells by extracts from *Mitragyna speciosa* (Korth) and mitragynine. *Natural Product Research*, 25(15), 1379-1387.

Raffa, R. B. (2014). Kratom and Other Mitragynines. In R. B. Raffa, *The Chemistry and Pharmacology of Opioids from a Non-Opium Source*. Boca Raton: CRC Press Taylor & Francis Group.

Ramanathan, S., & Mansor, S. M. (2014). Toxicology of Mitragynine and analogues. In S. Ramanathan, S. M. Mansor, & R. B. Raffa (Ed.), *The Chemistry and Pharmacology of Opioids from a Non-Opium* (1st ed., pp. 281-292). CRC Press.

Ramanathan, S., Parthasarathy, S., Murugaiyah, V., Magosso, E., Tan, S. C., & Mansor, S. M. (2015). Understanding the Physicochemical Properties of Mitragynine, a Principal Alkaloid of *Mitragyna speciosa*, for Preclinical Evaluation. *Molecules*, 20, 4915-4927. doi:10.3390/molecules20034915

Robson, P. (2001). Therapeutic aspects of cannabis and cannabinoids. *The British Journal of Psychiatry*, 178, 107-115. Retrieved from http://www.ukcia.org/research/Thereputic/Therapeut.htm#35

Sabetghadam, A., Ramanathan, S., Sasidharan, S., & Mansor, S. M. (2013). Subchronic exposure to mitragynine, the principal alkaloid of *Mitragyna speciosa*, in rats. *J. Ethnopharmacol*, 146, 815-823. doi:10.1016/j.jep.2013.02.008

Sallan, S. E., Zinberg, N. E., & Frei, E. (1975). Antiemetic effect of delta-9-tetrahydrocannabinol in patients receiving cancer chemotherapy. *New England Journal of Medicine*, 293, 795-797.

Shaik Mossadeq, W. M., Sulaiman, M. R., Tengku Mohamad, T. A., Chiong, H. S., Baharuldin, M. T. H., Israf, D.A., M. T., Baharuldin, M. T., & Israf, D. A. (2009). Anti-inflammatory and antinociceptive effects of *Mitragyna speciosa* Korth methanolic extract. *Medical Principles and Practice*, 18, 378-384.

Suwanlert, S. (1975). A study of kratom eaters in Thailand. *Bulletin on Narcotics,* 27(3), 21-27.

Symonds, C., & Berman, J. (2003). U.S. Pat. No. 20,060, 135,599.

Takayama, H. (2014). U.S. Pat. No. 15,032,070.

Thompson, G. R., Rosenkrantz, H., Schaeppi, U. H., & Braude, M. C. (1973). Comparison of acute oral toxicity of cannabinoids in rats, dogs and monkeys. *Toxicology and Applied Pharmacology,* 25, 363-372.

Thuan, L. C. (1957). Addiction to *Mitragyna speciosa. Proceedings of the Alumni Association,* 10, 322-324.

Trakulsrichai, S., Tongpo, A., Sriapha, C., Wongvisawakorn, S., Rittilert, P., Kaojarern, S., & Wananukul, W. (2013). Kratom abuse in Ramathibodi Poison Center, Thailand: a five-year experience. *J Psychoactive Drugs.* 2013 November-December; 45(5), 45(5), 404-8. doi:10.1080/02791072.2013.844532

Trakulsrichai, S., Sathirakul, K., Auparakkitanon, S., Krongvorakul, J., Sueajai, J., Noumj ad, N., . . . Wananukul, W. (2015). Pharmacokinetics of mitragynine in man. *Drug Des Devel Ther,* 9, 2421-2429. doi:10.2147/DDDT.S79658

Tsuchiya, S., Miyashita, S., Yamamoto, M., Horie, S., Sakai, S. I., Aimi, N., . . . Watanabe, K. (2002). Effect of mitragynine, derived from Thai folk medicine on gastric acid secretion through opioid receptor in anesthetized rats. *European of Pharmacology,* 443, 185-188.

Vicknasingam, B., Narayanan, S., Beng, G. T., & Mansor, S. M. (2010). The informal use of ketum (*Mitragyna speciosa*) for opioid withdrawal in the northern states of peninsular Malaysia and implications for drug substitution therapy. *Int. J Drug Policy,* 21, 283-288. doi:10.1016/j.drugpo.2009.12.003

Vicknasingam, B., Narayanan, S., Beng, G., & Mansor, S. (2010). The informal use of ketum (*Mitragyna speciosa*) for opioid withdrawal in the northern states of peninsular Malaysia and implications for drug substitution therapy. *Int J Drug Policy,* 21(4), 283-8. doi:10.1016/j.drugpo Wade, D. T., Makela, P. M., House, H., Bateman, C., & Robson, P. (2006). Long-term use of a cannabis-based medicine in the treatment of spasticity and other symptoms in multiple sclerosis. *Multiple Sclerosis,* 12, 639-645. Retrieved from http://files.iowamedicalmarijuana.org/science/ms/Wade %20Sativex %20MS %20Spasticity %20SAFEX %20MS %202006.pdf Yamamoto, L. T., Horie, S., Takayama, H., Aimi, N., Sakai, S., Yano, S., . . . Watanabe, K. (1999). Opioid receptor agonistic characteristics of mitragynine pseudoindoxyl in comparison with mitragynine derived from Thai medicinal plant *Mitragyna speciosa. Gen Pharmacol.,* 33(1), 73-81.

What is claimed is:

1. An emulsion or a capsule consisting essentially of:
   a) three or more selected from the group consisting of gelatin, hypromellose, pullulan, cellulose, carrageenan, polyethylene glycol, tocopherol, benzalkonium chloride, chlorobutanol, thiomersal, butylated hydroxy anisole, butylated hydroxytoluene, polysorbate, sorbitol, sorbitan, sorbitan monolaurate, sorbitan monostearate, sorbitan tristearate, glycerol monostearate, glycerol monolaurate, decyl glucoside, lauryl glucoside, octyl glucoside, amine oxide, octaethylene glycol monododecyl ether, pentaethylene glycol monododecyl ether, sodium alginate, polyoxypropylene, polyoxyethylene, polyoxyethylene cetylether, glycerol ester, glycerol, glyceride, xanthan gum, arabic gum, castor wax, candelila wax, chitosan, polyhydroxy aldehyde, polyhydroxy ketone, propylene glycol monolaurate, caprylic/capric/diglyceryl succinate, methyl paraben, ethyl paraben, propyl paraben, and poloxamer;
   b) a component selected from the group consisting of turpentine oil, soybean oil, sesame oil, castor oil, peanut oil, palm oil, orange oil, olive oil, nutmeg oil, mentha spicata oil, lime oil, lemon oil, lavender oil, lanolin oil, cottonseed oil, sunflower oil, corn oil, eucalyptus oil, coriander oil, coconut oil, clove oil, cinnamon oil, apricot kernel oil, anis oil, peppermint oil, arachis oil, jojoba oil, almond oil, polymerized siloxane and mixtures thereof;
   c) an isolated mitragynine, an isolated 7-hydroxymitragynine or an isolated mitragynine psedoindoxyl; and
   d) an isolated tetrahydrocannabinol or an isolated cannabidiol, wherein the emulsion or capsule is stable for at least 12 months such that at least 89% by mass of the emulsion or capsule remains in undegraded form after exposure to storage conditions with an ambient temperature of about 25° C. and a relative humidity of about 55%.

\* \* \* \* \*